United States Patent
Katz et al.

(10) Patent No.: US 12,300,034 B2
(45) Date of Patent: May 13, 2025

(54) PHYSICAL ACTIVITY MEASUREMENT AND ANALYSIS

(71) Applicant: 6Degrees Ltd., Tel Aviv-Jaffa (IL)

(72) Inventors: Aryeh Haim Katz, Tel Aviv (IL); Miri Berger Katz, Tel Aviv (IL)

(73) Assignee: 6DEGREES LTD., Tel-Aviv (IL)

( * ) Notice: Subject to any disclaimer, the term of this patent is extended or adjusted under 35 U.S.C. 154(b) by 0 days.

(21) Appl. No.: 18/461,324

(22) Filed: Sep. 5, 2023

(65) Prior Publication Data
US 2024/0221427 A1    Jul. 4, 2024

Related U.S. Application Data

(63) Continuation of application No. 16/279,254, filed on Feb. 19, 2019, now Pat. No. 11,783,634, which is a
(Continued)

(51) Int. Cl.
*G06V 40/20* (2022.01)
*A61B 5/11* (2006.01)
(Continued)

(52) U.S. Cl.
CPC ............ *G06V 40/23* (2022.01); *A61B 5/1118* (2013.01); *A63B 24/0062* (2013.01);
(Continued)

(58) Field of Classification Search
CPC .... A63B 2024/0009; A63B 2024/0012; A63B 2024/0015; A63B 2024/0021; A63B 2024/0025; A63B 2024/0068; A63B 24/0003; A63B 24/0006; G06V 40/20; G06V 40/23
See application file for complete search history.

(56) References Cited

U.S. PATENT DOCUMENTS

| | | | |
|---|---|---|---|
| 7,090,650 B2 * | 8/2006 | Ou | A61H 1/0277 601/5 |
| 7,220,220 B2 | 5/2007 | Stubbs et al. | |

(Continued)

FOREIGN PATENT DOCUMENTS

| | | | | |
|---|---|---|---|---|
| EP | 2162197 B1 * | 3/2011 | | A63B 21/0004 |
| WO | WO-2013/028581 A1 | 2/2013 | | |

OTHER PUBLICATIONS

The Extended European Search Report for European Patent Application No. 16913471.5, Jun. 24, 2020, EPO, Munich, Germany.
(Continued)

*Primary Examiner* — Steven J Hylinski
(74) *Attorney, Agent, or Firm* — GOODWIN PROCTER LLP

(57) ABSTRACT

A method of physical activity measurement and analysis, the method comprising computer-executed steps of: receiving at least one value extracted from measurements of a physical activity of a first user, and detecting a deviation of the physical activity of the first user from at least one previous physical activity using the received at least one value and at least one reference value calculated over at least one value extracted from measurements of the at least one previous physical activity.

20 Claims, 5 Drawing Sheets

Related U.S. Application Data continuation of application No. PCT/IB2016/056178, filed on Oct. 14, 2016.

(60) Provisional application No. 62/376,916, filed on Aug. 19, 2016.

(51) Int. Cl.
*A63B 24/00* (2006.01)
*G06F 18/2433* (2023.01)
*A61B 5/00* (2006.01)

(52) U.S. Cl.
CPC .......... *G06F 18/2433* (2023.01); *G06V 40/20* (2022.01); *A61B 5/1107* (2013.01); *A61B 5/6804* (2013.01); *A61B 2560/045* (2013.01); *A63B 2024/0068* (2013.01)

(56) References Cited

U.S. PATENT DOCUMENTS

| | | | |
|---|---|---|---|
| 7,402,125 B2 | 7/2008 | Wang | |
| 8,460,001 B1 | 6/2013 | Chuang | |
| 8,480,541 B1 | 7/2013 | Brunts | |
| 8,784,274 B1 | 7/2014 | Chuang | |
| 9,418,509 B2 | 8/2016 | Case, Jr. et al. | |
| 9,474,955 B2 | 10/2016 | Cobbett et al. | |
| 9,523,704 B2 | 12/2016 | Balakrishnan et al. | |
| 9,875,400 B2 | 1/2018 | Uchida et al. | |
| 10,019,806 B2 | 7/2018 | Perry et al. | |
| 10,049,595 B1 | 8/2018 | Chuang | |
| 10,368,744 B1 | 8/2019 | Miller et al. | |
| 11,263,919 B2 | 3/2022 | Malhotra | |
| 2002/0114493 A1 | 8/2002 | McNitt et al. | |
| 2004/0127821 A1* | 7/2004 | Ou | A61H 1/024 601/5 |
| 2006/0204045 A1 | 9/2006 | Antonucci | |
| 2008/0096726 A1 | 4/2008 | Riley et al. | |
| 2008/0249736 A1 | 10/2008 | Prstojevich | |
| 2009/0298650 A1 | 12/2009 | Kutliroff | |
| 2012/0253485 A1 | 10/2012 | Weast et al. | |
| 2012/0289296 A1 | 11/2012 | Marty et al. | |
| 2013/0128022 A1 | 5/2013 | Bose et al. | |
| 2013/0197680 A1 | 8/2013 | Cobbett et al. | |
| 2015/0120025 A1 | 4/2015 | Wisbey et al. | |
| 2015/0366518 A1 | 12/2015 | Sampson | |
| 2016/0322078 A1 | 11/2016 | Bose et al. | |
| 2017/0004358 A1 | 1/2017 | Bose et al. | |

OTHER PUBLICATIONS

A Partial Supplementary European Search Report for European Patent Application No. 16913471.5, Mar. 18, 2020, EPO, Munich, Germany.
The International Search Report and The Written Opinion for PCTIB2016/056178, Date of Mailing: Feb. 8, 2017.
First Foreign Office Action for European Application No. 16913471. 5, dated: Jul. 14, 2021, European Patent Office.

* cited by examiner

PHYSICAL ACTIVITY MEASUREMENT AND ANALYSIS

CROSS-REFERENCE TO RELATED APPLICATIONS

This application is a continuation of U.S. application Ser. No. 16/279,254 filed on Feb. 19, 2019, which is a continuation of International Application No. PCT/IB2016/056178 filed on Oct. 14, 2016, which claims the benefit of U.S. Provisional Application No. 62/376,916 filed on Aug. 19, 2016, the contents of which are hereby incorporated by reference herein in their entireties.

FIELD AND BACKGROUND OF THE INVENTION

The present invention relates to physical activity measurement and more particularly but not exclusively, to a system and method of physical activity measurement and analysis.

Many devices are currently used for measuring physical activities of a user. Most of those devices however, are used for tracking caloric aspects of physical activity, and are suitable for use by regular people only (say by users who jog daily, before going to work at their office).

Those devices have usually been limited to counting the user's steps or measuring the user's heart pulse rate, and rarely ever address any other aspect of a physical activity of a user.

Further, those devices are not tailored for the specific needs of a user who happens to be a professional athlete or a person who suffers from a motor disorder such as Parkinson's Disease, Essential Tremor, etc.

Indeed, such a user may need very different ways of measurements and analysis of her physical activities, for deriving relevant information from the measurements and analysis.

Further, for many physical activities, step counting and the measurement of pulse rate are either irrelevant, or simply not enough.

For example, sport physical activities such as Biking, Swimming, Boxing, Skiing or daily physical activities such as writing, operating a computer mouse, resting (say sitting), etc., may require alternative or additional ways of measurement and analysis, for deriving relevant information therefrom.

SUMMARY OF THE INVENTION

According to a first aspect of the present invention there is provided a method of physical activity measurement and analysis, the method comprising computer-executed steps of: receiving at least one value extracted from measurements of a physical activity of a first user, and detecting a deviation of the physical activity of the first user from at least one previous physical activity using the received at least one value and at least one reference value calculated over at least one value extracted from measurements of the at least one previous physical activity.

According to a second aspect of the present invention there is provided an apparatus for physical activity measurement and analysis, comprising: at least one computer processor, a value receiver, implemented on the computer processor, configured to receive at least one value extracted from measurements of a physical activity of a first user, and a deviation detector, in communication with the value receiver, configured to detect a deviation of the physical activity of the first user from at least one previous physical activity using the received at least one value and at least one reference value calculated over at least one value extracted from measurements of the at least one previous physical activity.

According to a third aspect of the present invention there is provided a non-transitory computer readable medium storing computer processor executable instructions for performing steps of physical activity measurement and analysis, the steps comprising: receiving at least one value extracted from measurements of a physical activity of a first user, and detecting a deviation of the physical activity of the first user from at least one previous physical activity using the received at least one value and at least one reference value calculated over at least one value extracted from measurements of the at least one previous physical activity.

Unless otherwise defined, all technical and scientific terms used herein have the same meaning as commonly understood by one of ordinary skill in the art to which this invention belongs. The materials, methods, and examples provided herein are illustrative only and not intended to be limiting.

Implementation of the method and system of the present invention involves performing or completing certain selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof.

For example, as hardware, selected steps of the invention could be implemented as a chip or a circuit. As software, selected steps of the invention could be implemented as a plurality of software instructions being executed by a computer using any suitable operating system.

In any case, selected steps of the method and system of the invention could be described as being performed by a data processor, such as a computing platform for executing a plurality of instructions.

BRIEF DESCRIPTION OF THE DRAWINGS

The invention is herein described, by way of example only, with reference to the accompanying drawings.

With specific reference being now made to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. The description taken with the drawings making apparent to those skilled in the art how the several forms of the invention may be embodied in practice.

In the drawings:

FIG. 1A is a simplified block diagram schematically illustrating a first exemplary apparatus for physical activity measurement and analysis, according to an exemplary embodiment of the present invention.

FIG. 1B is a simplified block diagram schematically illustrating a second exemplary apparatus for physical activity measurement and analysis, according to an exemplary embodiment of the present invention.

FIG. 2A is a simplified flowchart schematically illustrating a first exemplary method of physical activity measurement and analysis, according to an exemplary embodiment of the present invention.

FIG. 2B is a simplified flowchart schematically illustrating a second exemplary method of physical activity measurement and analysis, according to an exemplary embodiment of the present invention.

FIG. 3 is a block diagram schematically illustrating a non-transitory computer readable medium storing computer executable instructions for performing steps of physical activity measurement and analysis, according to an exemplary embodiment of the present invention.

DESCRIPTION OF THE PREFERRED EMBODIMENTS

Figure 1A:
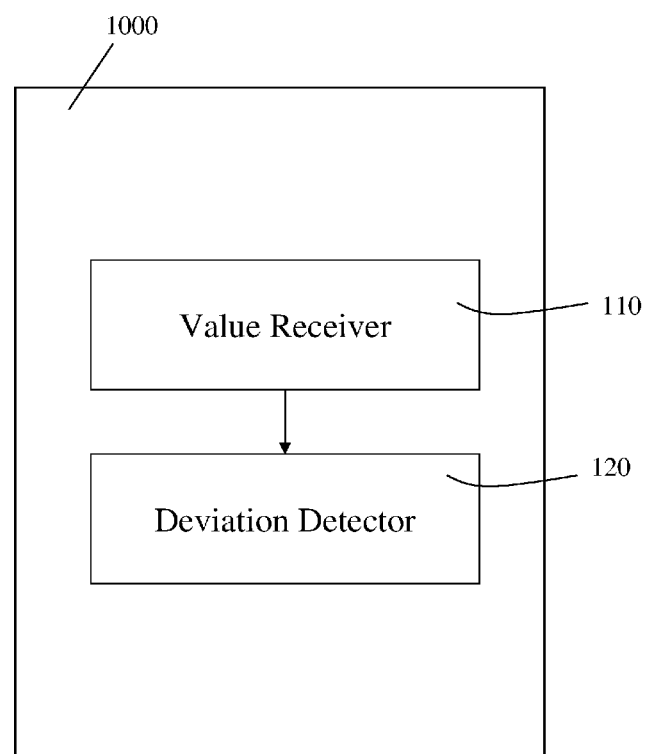

The present embodiments comprise an apparatus and a method of physical activity measurement and analysis.

According to some of the present embodiments, a physical activity of a user is analyzed in light of previously measured physical activities rather than based on the physical activity alone.

Further, according to some of the embodiments, an analysis of the user' physical activity may takes into consideration data on the user's physical condition (say illness) or ability, on the type of the physical activity (say biking, swimming, etc.), and data on previous physical activities of the same user, type, or user and type.

Thus, the user's performance during the physical activity may be understood in light of his own history of physical activities, a history of physical activities of a same type (say of biking, resting, etc), of similar activities by users who suffer from a same illness as the user's, etc., or any combination thereof.

Further, the history of the user's physical activities may serve as a basis for a tracking the user's condition, and for quantifying changes in the user's condition based on several physical activity sessions, say on a periodic (say daily) basis, as described in further detail hereinbelow.

Furthermore, according to some of the embodiments, for measuring the user's physical activity, movements that make up the physical activity are measured in more than one aspect (say by measuring both muscle pressure and body part orientation).

Thus, according to some embodiments, there is received one or more value extracted from measurements of a physical activity of a user, say by a computer in remote communications with a device used to measure the physical activity of the user, as described in further detail hereinbelow.

For example, a device worn by the user during a physical activity such as walking, running, and even resting, may include a computer processor and one or more sensors (say pressure meters, gyroscopes, GPS (Global Positioning System) Receivers, etc.) that are used for measuring the user's physical activity.

The device worn by the user may be used to measure the user's physical activity, for example by taking measurements of pressure applied by a muscle of the user upon contraction when extending an arm, by taking measurements of changes in angular orientation of a user's arm or foot, etc., during the physical activity.

According to one example, values extracted from the measurements of the physical activity may be used to detect a deviation of the physical activity from at least one previous physical activity by the user, from similar physical activities by other users, etc., as described in further detail hereinbelow.

The received one or more values may be used for detecting a deviation of the physical activity from at least one previous physical activity, using at least one reference value previously calculated over one or more values extracted from measurements of the previous physical activities.

Specifically, a comparison made between the received values and the reference values may show a deviation of the received values from the reference values.

The reference values are thus used as a kind of a "base level" for the values extracted from the measurements, as expected based on the one or more previous physical activities by the user or on similar physical activities by a group of users (say other athletes or users who suffer from a same disorder as the user's).

Optionally, each one of the reference value is a stand-alone, single value (say an average value), say a value calculated by averaging over measurements of pressures applied by muscles of the user's foot or upper arm during the previous physical activity (say during a previous session of training or of physiotherapy).

Alternatively, the previous physical activity (say biking) involves a repeated movement cycle and each one of the reference values pertains to a different time (say a different time frame) within the repeated cycle. The reference values may thus make up a set of values also referred to hereinbelow as an 'envelope' that represents "borderlines" within which the values extracted during one cycle of the physical activity are expected to stay.

In a first example, the user is a professional athlete and the detection of the deviation of the physical activity is based on reference values calculated over measurements made during one or more previous physical activities (say training sessions) of the athlete, say during a marathon or a bike cycling event.

In the first example, the detection of the deviation from the previous physical activity is a part of or a prerequisite for the computer's recognizing of a user's gesture with which the user controls the computer.

For example, a computer may be programmed to recognize a gesture predefined, say by an administrator or programmer (say a gesture used for commanding the computer to capture a picture of the user using a camera connected to the computer), based on the received values.

In the example, the gesture is defined by the programmer or administrator in a database, say as a set of value ranges that the received values have to be within, in order for a user's movement to be recognized as the gesture, associated with a computer command to be issued, as described in further detail hereinbelow.

However, according to exemplary embodiments, the gesture is recognized only when there is also detected a deviation of the user's physical activity from the previous physical activities of the user, as described in further detail hereinbelow.

More specifically, by determining if the received values deviate from a "base level" made of reference values calculated over the previous physical activities, the computer is able to decide if a user's movement during the physical activity is indeed, the predefined gesture or rather a movement expected for such a physical activity.

The computer may thus tell whether the user's movement is intended to be the predefined gesture or rather is a movement that—although similar to the gesture in direction, angle, etc.—is a normal part of the physical activity itself.

Optionally, upon construing the movement as the predefined gesture, there is issued the command to the computer (say a command to start a stopwatch, stop a stopwatch, capture an image of the user with a camera controlled by the computer, etc.), as described in further detail hereinbelow.

Thus, the present embodiments may allow automatic generation of computer commands based on measurements taken during a user's physical activity, and a "base level" made of reference values calculated from values extracted from measurements of previous physical activities by the user.

Additionally or alternatively, the detected deviation may be interpreted as indicating a change in the user's condition (as compared with previous physical activity of the same type, say previous sessions of biking by the user), as described in further detail hereinbelow.

In one example, the user is a person who suffers from Parkinson's disease. One of the symptoms of Parkinson's disease is tremor at rest. Even in early stages of the disease, most of the people who suffer from the disease experience tremor in the hand, foot, jaw, etc. The tremor consists of a shaking or oscillating movement, and usually appears when a person's muscles are relaxed, or are at rest, hence the term "tremor at rest".

In the example, the received values are extracted from measurements taken during a session in which the user rests. Thus, in the example, the measured physical activity is actually a one of resting (say of sitting or lying).

Further in the example, a computer (say a hospital computer) is programmed to recognize a movement of the user as a gesture (say a specific upper arm orientation used for instructing the hospital computer to call a nurse) predefined by a programmer, based on the received values, as described in further detail hereinbelow.

However, the computer further uses a reference value, to verify that the movement is not a part of the user's usual tremor at rest, before any recognition of the gesture, as described in further detail hereinbelow. To that end, the computer uses the reference value, for verifying that the movement causes the user's physical activity to deviate from the previous physical activities of the user during rest, before trying to recognize any gesture.

The reference value is a value calculated based on measurement taken from the user during previous sessions, as the user experiences tremor at rest, say by averaging over pressure and orientation measurements taken from the user during the previous sessions, as described in further detail hereinbelow.

Using a "base level" of tremors at rest, as represented by a reference value, the computer determines if a user's movement's is indeed intended be the gesture, or rather is an unintentional movement that—even if similar to the predefined gesture in direction, angle, etc.—is within limits of the tremor that the user usually experiences at rest.

Additionally or alternatively, the detected deviation from the "base level" of tremor at rest may be interpreted as indicating a change in the user's condition (say an alleviation of the user's tremor at rest symptoms), as described in further detail hereinbelow.

Thus, potentially, the present embodiments may also improve accuracy of automatic analysis of a physical activity based on measurements taken during the activity, by taking into consideration a "base level" made of previously calculated reference values that represents a user's history of physical activities.

The principles and operation of an apparatus and a method according to the present invention may be better understood with reference to the drawings and accompanying description.

Before explaining at least one embodiment of the invention in detail, it is to be understood that the invention is not limited in its application to the details of construction and the arrangement of the components set forth in the following description or illustrated in the drawings.

The invention is capable of other embodiments or of being practiced or carried out in various ways. Also, it is to be understood that the phraseology and terminology employed herein is for the purpose of description and should not be regarded as limiting.

Reference is now made to FIG. 1A, which is a simplified block diagram schematically illustrating a first exemplary apparatus for physical activity measurement and analysis, according to an exemplary embodiment of the present invention.

An exemplary apparatus 1000 for physical activity measurement and analysis, according to an exemplary embodiment of the present invention, may be implemented as a computer program, as hardware, as a combination of a computer program and hardware, etc.

The apparatus 1000 includes a computer. A computer as used hereinabove and hereinbelow, may be a single computer, or rather actually include two or more computers that are in a wired or wireless communication.

Optionally, the computer of apparatus 1000 is a server computer or any other computer that is a part of a client-server or cloud implemented system that includes apparatus 1000 as well one or more additional computers in communication therewith.

Optionally, the computer is a computer in use in a clinical environment (say at a physiotherapy clinic or at a hospital's department), a computer in use at a gym or at another sport facility, a computer in remote communication with that computer, etc., or any combination thereof, as described in further detail hereinbelow.

Optionally, the computer includes a user's computer such as a smart mobile phone, a tablet computer, or another computer in use by the user, a computer in remote communication with the user's computer, etc., or any combination thereof, as described in further detail hereinbelow.

Accordingly, the apparatus 1000 includes one or more computer processors, say one or more computer processors of a first computer (say a dedicated server computer at a gym or a user's smart mobile phone), one or more computer processors of a computer in remote communication with the first computer, or both.

The apparatus 1000 further includes one or more additional parts, say the parts denoted 110-120 in FIG. 1A, and possibly, other parts too, as described in further detail hereinbelow.

The additional parts may be implemented as software—say by programming one or more of the computer processors to execute the exemplary method described in further detail hereinbelow and illustrated using FIG. 2A, as hardware—say as an electric circuit that implements at least a part of the method, etc., or any combination thereof.

The apparatus 1000 further includes a value receiver 110, say a value receiver 110 implemented by programming the computer of the apparatus 1000.

The value receiver 110 receives one or more values extracted from measurements of a physical activity of a first user, as described in further detail hereinbelow.

Optionally, for receiving the one or more values, the value receiver 110 communicates with a device used to carry out the measurements of the physical activity of the first user (say a device having a computer and one or more sensors), as described in further detail hereinbelow.

The physical activity may include, but is not limited to, walking, running, swimming, biking, skiing, rowing, skating, dancing, operating a mechanical device used for physiotherapy or for exercising in a gym, operating a computer mouse, resting (say sitting), etc., as described in further detail hereinbelow.

The measurements taken by the device may include, for example, measurements of physical parameters such as pressure applied by a muscle of the first user, orientation of the first user's foot or hand, etc. The measurements are taken during the physical activity of the first user, and are thus used for measuring the first user's physical activity in real time.

Optionally, the device measures the physical activity without direct contact with the first user's body (say using one or more cameras and an automatic image processing based analysis of the first user's movements during the physical activity, as known in the art).

Optionally, the measurements that the values received by the value receiver 110 are extracted from are rather taken by a device deployed on a body part of the first user during the physical activity, say a device worn on the first user's foot or arm during the first user's physical activity, as described in further detail hereinbelow.

In one example, the device includes a computer (say a smart phone) connected to one or more sensors (say pressure meters such as an FSR (Force Sensitive Resistor), a gyroscope, an accelerometer, an IMU (Inertial Measurement Unit), etc.) that are attached to the user's body and are used for measuring the physical activity.

In the example, the device worn by the first user is used to measure the first user's physical activity by taking measurements of pressure applied by muscle of the first user when extending an arm or a foot, measurements of angular orientation of the first user's arm or foot, etc., during the physical activity.

Optionally, the values received by the value receiver 110 include results of each measurement taken by the device (say the result of each measured pressure, orientation, etc., as taken by the device worn by the user).

Alternatively or additionally, the received values include values calculated by the device (say by the worn device's computer) from the results, say one or more averages calculated over the results, as described in further detail hereinbelow.

Thus, in one example, each one of the received values is an average calculated by the worn device from measurements taken during a respective three minutes period of the physical activity, from two or more measurements taken on the first user's body during the respective three minutes period.

The apparatus 1000 further includes a deviation detector 120 in communication with the value receiver 110, say a deviation detector 120 implemented by programming the computer of the apparatus 1000.

The deviation detector 120 may detect a deviation of the physical activity of the first user from at least one previous physical activity.

The deviation detector 120 detects the deviation using the received one or more values and one or more reference values calculated over at least one value extracted from measurements of the at least one previous physical activity, say according to a predefined criterion.

Optionally, the criterion is defined by an administrator or programmer of apparatus 1000 in advance of receiving the values, say as a part of setting up the apparatus 1000 using a dedicated GUI (Graphical User Interface), as described in further detail hereinbelow.

Optionally the criterion is specific to a user (say per username, ID number, etc.), to a physical activity type, to a combination of a user and a physical activity type, etc. Accordingly, the criterion may be selected automatically by the deviation detector 120, or rather manually (say by the administrator) before the values are received by the value receiver 110, as described in further detail hereinbelow.

Optionally, the criterion defines which reference value is to be used for determining if the first user's physical activity deviates from the previous physical activities, say from previous physical activities by the first user.

Optionally, the measurements of the previous physical activities are measurements taken on a body part of the first user during the previous physical activities, say using a device similar to the device worn by the user, as described in further detail hereinabove.

Thus, in a first example, the physical activity is one of working with a specific object (say a specific weight) in a gym, as known in art.

In the first example, before the first user starts working with the specific object, the apparatus 1000 automatically selects a criterion to be used for detecting a deviation from previous physical activities, say according to physical activity type (say a criterion defined for working with a weight).

According to the selected criterion, a deviation is detected when one of the values received by the value receiver 110 crosses a reference value that is a threshold value calculated by averaging over pressure values measured on a user's arm muscle during previous exercises of the user with the same object, and multiplying by 120%.

Thus, the criterion of the example is that the received value is at least 20% higher than the average of the pressure values measured on the user's arm muscle during the previous exercises (i.e. during the previous physical activities of the first example).

Optionally, the physical activity involves a repeated cycle of movement, and each one of the reference values pertains to a different time (say a different time frame) within the repeated cycle of movement.

Thus, in one example, the physical activity is an indoor cycling session taken by the first user, and the previous physical activities are previous indoor cycling sessions taken by the first user.

In the example, the deviation detector 120 detects the deviation when one of the values received by the value receiver 110 is out of an "envelope" made of reference values calculated over the previous indoor cycling sessions taken by the first user, as described in further detail hereinbelow.

Optionally, the one or more reference values are values calculated over a plurality of values extracted from measurements of physical activities of a plurality of users, say over values extracted from measurements taken during previous physical activities of a same type, by other users or by both the first user and other users.

Thus, in one example, the physical activity is one of exercising using an object (say a weight) or a device (say a rowing machine) in a gym or a at physiotherapy clinic, and the reference values are calculated over values extracted from measurements of previous exercises by two or more users using that object or device.

Optionally, the apparatus 1000 further includes a command generator (not shown) in communication with the deviation detector 120, say a one implemented by programming the computer of apparatus 1000.

Optionally, upon the detection of the deviation by the deviation detector 120, the command generator issues a command predefined by a programmer or administrator of apparatus 1000, to the computer of the apparatus 1000, as described in further detail hereinbelow.

Optionally, the command is defined by an administrator or programmer of apparatus 1000, say as a part of the criterion for detecting the deviation, as described in further detail hereinbelow.

Optionally, the apparatus further includes a gesture recognizer (not shown), in communication with the deviation detector 120, say a one implemented by programming the computer of apparatus 1000.

Only when the deviation detector 120 detects the deviation, are the values received by the value receiver 110 forwarded to the gesture recognizer, for determining whether the received values represent a gesture predefined by a programmer or administrator of apparatus 1000.

Optionally, for defining the gesture, there are defined ranges of values (say ranges of pressure values, orientation values, etc.) that the received values have to be within, in order for the gesture recognizer to recognize a user's movement made during the physical activity, as the gesture.

Optionally, for defining the gesture, there are defined threshold values (say of pressure values, orientation values, etc.) that the received values have to cross, in order for the gesture recognizer to recognize a user's movement made during the physical activity, as the gesture.

The value ranges, threshold values, or both, may be defined by a programmer or administrator of apparatus 1000, and stored in a database of gesture definitions, as described in further detail hereinbelow.

Optionally, the programmer or administrator further defines a command that the gesture is meant to trigger the issuance of, to be stored in the database of gesture definitions, as a part of the gesture's definition, as described in further detail hereinbelow.

Apparatus 1000's command generator may be in communication with the gesture recognizer, or rather with both the deviation detector 120 and the gesture recognizer.

Optionally, upon detection of the deviation by the deviation detector 120, the command generator issues a command to the computer—say a control instruction for turning on a camera controlled by the computer, a computer command that moves a graphical object or otherwise updates content presented on a screen of a headset used for virtual reality, augmented reality, etc., as know in the art.

Alternatively, the command generator issues the command only when in addition to the detection of the deviation, the gesture recognizer recognizes a predefined gesture that the user or administrator defines as meant to trigger the issuance of the command, as described in further detail hereinabove.

Thus, in one example, the first user wears a device that uses a pressure meter (say an FSR strip), an orientation measurer (say an IMU), or both, to extract the values later received by the value receiver 110, by measuring pressure applied by a muscle on a body part of the first user and an orientation of that body part.

In the example, when the first user performs a predefined gesture such as a muscle operation or change in orientation of the body part, the received values extracted from the measured pressure applied by the muscle and the orientation of the body part are used to recognize the gesture performed by the first user.

Subsequently, the command generator issues the command based on the gesture's being recognized by the gesture recognizer.

However, in the example, only when the deviation detector 120 detects the deviation of the first user's physical activity from the previous physical activities, are the received values forwarded to the gesture recognizer.

Thus, in the example, only a movement with which the physical activity deviates from the previous physical activities may be recognized as the predefined gesture and as a result, trigger the issuance of the command to the computer, as describe in further detail hereinbelow.

Optionally, the apparatus 1000 further includes a user condition indicator (not shown), in communication with the deviation detector 120, say a one implemented by programming the computer of apparatus 1000, as described in further detail hereinabove.

The user condition indicator may determine that the deviation detected by the deviation detector 120 reflects a physical condition of the first user, say an improvement in the first user's performance (as compared with previous physical activity of the same type, say with previous sessions of biking by the first user).

When determining that the deviation reflects the condition, the user condition indicator further presents an indication, say as a textual message or as a graphical message, say on a screen of the computer of apparatus 1000 or on a website accessible over the internet by the first user or by his physician, etc.

Similarly, the user condition indicator may determine that the detected deviation reflects a medical condition—say an early stage of Parkinson's disease, say when a deviation detected by the deviation detector 120 pertains to resting. The user condition indicator may then present an appropriate textual message to a physician on a screen of the computer of apparatus 1000.

In a first example, the first user is a professional athlete and the detection of the deviation of the physical activity is based on reference values calculated over values extracted from measurements of previous physical activities of the first user, say of running sessions or marathons.

In the first example, the gesture recognizer recognizes a movement made by the first user during the physical activity as a gesture predefined, say by an administrator or programmer of apparatus 1000.

In the example, for implementing the gesture recognizer, the programmer programs the computer to recognize the gesture when a user's arm aligns into a specific lateral orientation and immediately following that alignment, a pressure is applied by the user's arm muscle in a specific direction.

The predefined gesture of the example is used by the first user for commanding the computer to capture a picture of the first user, say using a camera connected to the computer, to start or stop a stopwatch, etc., as described in further detail hereinabove.

In the example, rather than being conditioned upon the received values only, the command is issued only if both a deviation from a 'base level' represented by the reference values is detected by the deviation detector 120, and the predefined gesture is recognized by the gesture recognizer.

That is to say that the gesture recognizer recognizes the first user's movement as the predefined gesture, only if with that movement, the physical activity of the first user deviates from the previous physical activities by the first user.

Indeed, as described in further detail hereinabove, only when the physical activity deviates from the previous physical activities, are the values forwarded to the gesture recognizer.

Thus, a movement of the first user that does not make the first user's physical activity deviate from the previous physical activities, even when similar to the predefined gesture (say when the received values are within ranges predefined for the gesture), is interpreted as a part of the physical activity itself rather than the gesture.

Thus, in a one exemplary case, the physical activity is biking.

In the exemplary case, the gesture recognizer recognizes a rotational movement of the first user's foot as a predefined rotational gesture only if additionally, a received value extracted from the measurements taken during the rotational movement (and therefore the physical activity) deviates from the reference values.

In this biking example, the reference values are calculated based on values extracted from measurements taken during previous biking activities of the user, as described in further detail hereinbelow.

In a second example, the user is a person who suffers from Parkinson's disease.

One of the symptoms of Parkinson's disease is tremor at rest, as described in further detail hereinabove.

In the second example, the values that are received by the value receiver 110 are values extracted from measurements taken during a session in which the first user rests, thus in the example, the measured physical activity is actually a one of resting (say of sitting or lying).

Only when the deviation detector 120 detects a deviation based on the received values and a reference value, does the deviation detector 120 forwards the received values to the gesture recognizer.

In the example, using the received values forwarded by the deviation detector 120, the gesture recognizer may recognize a gesture predefined, say by an administrator or programmer, say a gesture characterized by a specific orientation of the first user's arm and a pressure applied by the arm's muscle at a specific direction.

In the example, the gesture's definition by an administrator or programmer of apparatus 1000 includes a command that causes the computer to call the nurse, thus the gesture may be used by the first user to instruct the computer to call the nurse, as described in further detail hereinbelow.

Further in the example, the reference value is a value calculated based on values extracted from measurements taken from the first user during previous sessions, as the first user experiences tremor at rest, say by averaging over pressure and orientation measurements taken during the previous sessions.

In one case, based on a user-specific criterion predefined by an administrator or programmer of apparatus 1000, when one of the values received during the rest is more than 10% larger than the reference value, the deviation detector 120 detects a deviation of the physical activity from the previous physical activities.

Following the detection of the deviation, the deviation detector 120 forwards the received values to the gesture recognizer, and the gesture recognizer determines if the received values represent the predefined gesture.

However, in the example, it is assumed that with an unintentional movement that is a part of the first user's usual tremor at rest, even when the movement is similar to the gesture in direction, angle, pressure applied by muscle, etc., none of the received values is likely to be more than 10% larger than the reference value.

Thus, when staying within 10% difference from the reference value, the unintentional movement does not make the physical activity deviate from the first user's previous physical activities of rest. As a result, the received values are not forwarded to the gesture recognizer, and the unintentional movement is effectively construed as a one that is within the limits of the tremor usually experienced by the first user at rest and that therefore, should not be construed to be the predefined gesture.

Further in the example, a detected deviation from the "base level" of tremor at rest as represented by the reference value, may be interpreted as indicating a condition of the first user (say an alleviation of the tremor at rest symptoms after administration of a particular drug), as described in further detail hereinbelow.

The apparatus 1000 may thus potentially help track changes in the first user's condition on a day to day basis, as well as throughout a long period of treatment.

Optionally, the apparatus 1000 further includes a reference value calculator (not shown) in communication with the deviation detector 120, the value receiver 110, or both, say a one implemented by programming the computer of apparatus 1000, as described in further detail hereinabove.

The reference value calculator calculates the reference value from previously received values extracted from measurements of one or more previous physical activities, say by averaging over the previously received values.

Optionally, the apparatus 1000 further includes a database of reference values (say a database implemented on a memory of the computer of the apparatus 1000), and the reference value calculator stores the calculated reference values in the database of reference values, as described in further detail hereinbelow.

Optionally, the database of reference values further includes a vocabulary of physical activity types. The vocabulary defines for each one of the physical activity types, one or more types of reference values that need to be calculated.

In one example, the vocabulary defines that for biking, there needs to be calculated a series of value ranges (i.e. reference values) that make up an "envelope", say by running a linear regression or another linear approximation method on the values extracted from the previously measured physical activities.

In the example, the vocabulary further defines that for jogging, there rather needs to be calculated a single, stand-alone reference value by averaging over values extracted from the previously measured physical activities.

Optionally, the reference value calculator further updates one or more of the reference values based on the values extracted from the measurements of the physical activity of the first user and received by the value receiver 110, and stores the updated one or more reference values in the database of reference values.

Thus, in one example, the reference value used for detecting the deviation is an average of physical pressure values measured during previous physical activities performed by the first user. In the example, the reference value is recalculated based on both the values received by the value receiver 110 and the value of the reference value prior to the receipt of the values by the value receiver 110, as described in further detail hereinbelow.

According some of the present embodiments, a reference value may be calculated per user, per physical activity type, per user and physical activity type, etc.

Accordingly, in a first example, the database of reference values is a user-specific database dedicated to the first user only. In the example, the reference values in the database are accessible according to the type of physical activity (say running, rowing, resting, etc.), say using indexes, primary keys, foreign keys, etc., as known in the art of computer database design.

In a second example, the database of reference values is not user-specific and rather holds reference values of more than one user. The non user-specific database is accessible according to physical activity type (say running, walking, resting, etc.), user, or a combination of user and physical activity type, say using indexes, primary keys, foreign keys, etc., as known in the art of computer database design.

Optionally, the apparatus 1000 further includes a database of detected deviations (say a database implemented on a memory of the computer of the apparatus 1000), and the deviation detector 120 stores data on previously detected deviations in the database of detected deviations.

Optionally, the database of detected deviations holds only data that pertains to the first user, and is thus a personal, user-specific database that is dedicated to the first user only.

In one example, the data in the database of detected deviations that is dedicated to the first user only, is accessible according to the type of physical activity (say running, walking, resting, etc.), say using indexes, primary keys, foreign keys, etc., as known in the art of computer database design.

Optionally, the database of detected deviations holds data that pertain to two or more users, and is thus not user-specific.

In one example, the data in the database of detected deviations that is not user-specific, is accessible according to a type of physical activity (say running, resting, etc.), a user, or a combination of user and activity type, say using indexes, primary keys, foreign keys, etc., as known in the art.

Optionally, following any detection of a deviation by the deviation detector 120, the deviation detector 120 updates the database of detected deviations with a database record that holds data on the detected deviation.

In one example, the database record holds the received values extracted from the measurements of first user's physical activity, one or more reference values used for detecting the deviation, and a degree of deviation (say a difference or ratio calculated between the former two), etc.

In the example, the degree of deviation may be calculated, for example, by subtracting the reference value from one of the received values, by dividing the received value by the reference value, etc., as described in further detail hereinbelow.

Optionally, the apparatus 1000 further includes a deviation evaluator (not shown), in communication with the deviation detector 120, the database of detected deviation, or both the deviation detector 120 and the database. Optionally the deviation evaluator is implemented by programming the computer of apparatus 1000, as described in further detail hereinabove.

The deviation evaluator compares to the deviation detected by the deviation detector 120 to the data stored in the database of detected deviations, for evaluating the detected deviation using the data on the previously detected deviations.

For example, when the first user is a patient who suffers from a motor disorder, the detected deviation may be compared to data on deviations detected previously for that first user (say using the degrees of deviation), so as to track the progress of the first user, as described in further detail hereinbelow.

Optionally, the deviation evaluator further updates reference values, criterions, etc., in light of the comparison made with the data on the previously detected deviations, say by conditioning a re-calculation of a reference value upon a trend of change in the deviation's degree, as described in further detail hereinbelow.

Thus, in one example, the deviation evaluator updates a criterion used by deviation detector 110 in light of a trend made of a sequence of three increases in the deviation's degree, say by lowering a percentage difference from a reference value needed, according to the criterion, for a deviation be detected.

By updating the criterion, the deviation evaluator further adjusts a sensitivity of apparatus 1000 to the values received by the value receiver 110 (and thus to the measurements) in light of the evaluation of the deviations detected by the deviation detector 120. Thus, for example, the sensitivity may be made higher when the detected deviations appear to weaken over time (say when the deviation's degree appears to decrease).

Figure 1B:
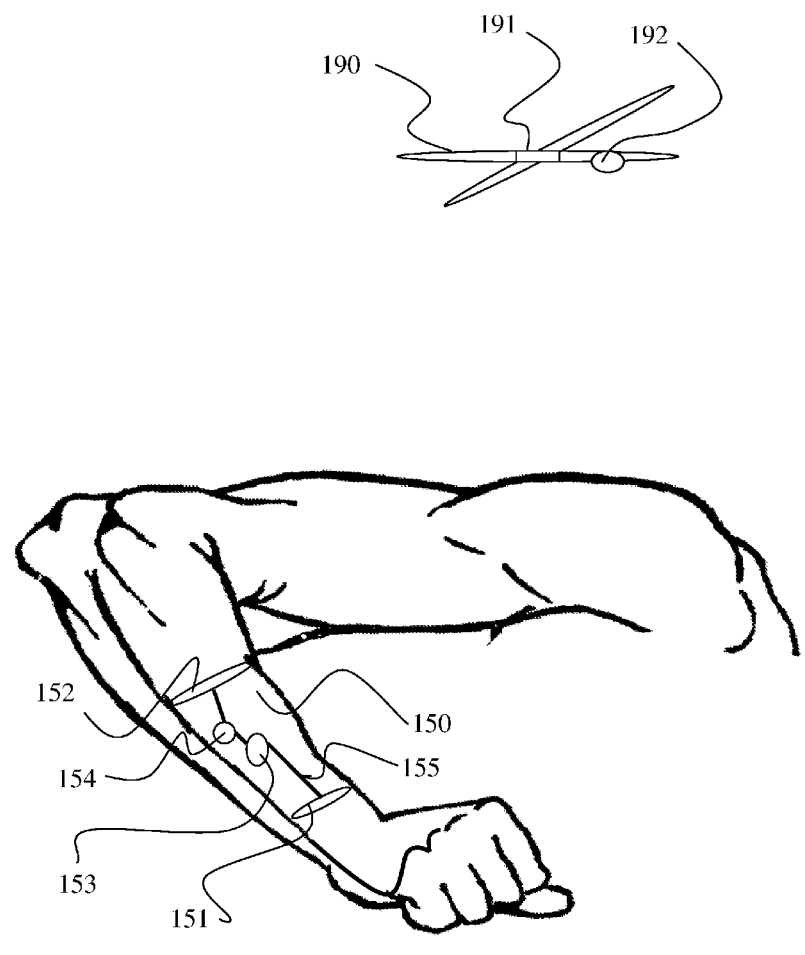

Reference is now made to FIG. 1B, which is a simplified block diagram schematically illustrating a second exemplary apparatus for physical activity measurement and analysis, according to an exemplary embodiment of the present invention.

A second exemplary apparatus according to an exemplary embodiment of the present invention includes the apparatus 1000 of FIG. 1A, a measurement device adapted to be worn on a user's arm 150, and a physical activity monitoring device, as described in further detail hereinbelow.

In one example, the measurement device is embedded in a shirt worn on by a user, such that when the user wears the shirt, the measurement device components 151-154 are deployed on the user's arm 150. The components 151-154 are connected by an electrically circuit 155 which is implemented using conductive fibers embedded in the shirt—say using thin metal strands woven into the construction of the shirt's textile.

In a second example, the components 151-154 are rather embedded in a strap that may be worn on the user's arm 150.

The measurement device includes one or more sensors, say a pressure meter 152—such as a Force Sensing Resistor (FSR), an orientation measurer 151—such as a gyroscope, a GPS Receiver, a Differential GPS Receiver, etc., or any combination thereof, as described in further detail hereinbelow.

Optionally, the sensors include one or more pairs of pressure meters 152 which are arranged on the shirt or strap, such that when worn by the user, each two pressure meters 152 of a pair are deployed on opposite sides of a preferable area of the user's arm 150.

In one example, the pair of pressure meters 152 is positioned over opposite sides of the arm's 150 muscle and serve as control references for each other, as providers of complementary information, etc.

Similarly, the sensors may include one or more pairs of orientation measurers 151 that are arranged on the shirt or strap, such that when worn by the user, each two orientation measurers 151 of a pair are deployed on preferable areas of the arm 150, say on areas positioned over opposite sides of the arm's 150 muscle.

Optionally, the two orientation measurers 151 serve as control references for each other, as providers of complementary information, etc.

The measurement device further includes a computer processor 153, connected to the sensors.

The computer processor 153 is configured (say by programming) to use the sensors for measuring a physical activity of the user, by taking measurements of pressure applied by the arm's 150 muscle, by taking measurements of the arm's orientation, etc., as described in further detail hereinabove.

The computer processor 153 is further configures (say by the programming), to extracts values from the measurements taken using the sensors and to forward the extracted values to apparatus 1000, as described in further detail hereinabove.

The computer processor 153 may include, but is not limited to: a microprocessor, a microcontroller (typically having a processing unit as well as a fixed amount of RAM, ROM and other peripherals, embedded on a single chip), etc.

The computer processor 153 may also include, but is not limited to another hardware component (say an integrated circuit) capable of using the sensors for taking the measurements and for performing calculations based on the measurements, in order to extract the values from the measurements.

The measurement device further includes a data transmitter 154 also embedded in the shirt or strap. The data transmitter 154 is connected to the computer processor 153 (say by the electrical circuit 155 which is implemented using conductive fibers embedded in the shirt, or through another wired or wireless connection, as known in the art).

Optionally, apparatus 1000 is implemented on the physical activity monitoring device, and the data transmitter 154 transmits the extracted values over a wireless (say using Bluetooth®) or wired connection, to the physical activity monitoring device, say to the value receiver 110, as described in further detail hereinbelow.

Alternatively, apparatus 1000 is rather implemented on the measurement device itself, say on the computer processor 153, and the data transmitter 154 rather transmits control instructions issued by the apparatus 1000 to the physical activity monitoring device, as described in further detail hereinbelow.

The physical activity monitoring device may include one or more hardware and/or software components.

In one example, the physical activity monitoring device includes a vehicle 190—say an aerial vehicle 190 such a quadcopter.

In the example, the physical activity monitoring device further includes a controller 191 deployed on the vehicle 190, for controlling the movement of the vehicle 190—say as a programmed microchip 191 that controls the aerial vehicle's 190 rotor engines, wings, etc., as known in the art.

The controller 191 maneuvers the vehicle 190 based the control instructions, as known in the art.

Optionally, the control instructions are issued by the apparatus 1000 (when implemented on the measurement device) and are wirelessly transmitted to the controller 191 by the data transmitter 154, as described in further detail hereinabove.

Alternatively, the control instructions are issued by the apparatus 1000 on the physical activity monitoring device itself (when the apparatus 1000 is implemented thereon), as described in further detail hereinabove.

In the example, the physical activity monitoring device further includes other components.

The other components may include, but are not limited to: a camera 192—for capturing stills and/or video images of the user, a microphone—for capturing audio signals (say for allowing the user to vocally comment on events, in real time, during the physical activity), etc., or any combination thereof.

The components of the physical activity monitoring device may alternatively or additionally include a stopwatch, a timer, a data storage (say a flash memory), a cellular modem (say for forwarding the images and vocal comments, live to a remote computer), etc., or any combination thereof.

By moving his arm 150 in a specific way (say by aligning the arm in a specific orientation) as per a gesture predefined by a programmer of apparatus 1000, the user may control the physical activity monitoring device, using control instructions issued by the apparatus 1000 upon recognition of the arm's 150 movement as the gesture.

However, in order to avoid erroneous recognition of an unintentional movement of the arm or of a movement that is a natural part of a physical activity performed by the user, as the predefined gesture, the movement of the arm 150 must also make the physical activity deviate from previous physical activities of the user.

To that end, the deviation detector 120 of apparatus 1000 forwards the values extracted from the measurements taken using the sensors to apparatus 1000's gesture recognizer only when detecting a deviation of the physical activity from the previous physical activities of the user, as described in further detail hereinabove.

Thus, in one example, a user rafting in a canoe and wearing a suit in which the measurement device with the above described pressure meter 152, orientation measurer 151, computer processor 153 and data transmitter 154, are embedded, is allowed to control the physical activity monitoring device.

In the example, the physical activity monitoring device includes a quadcopter 190, a video camera 192, and a controller 191 which controls both the quadcopter 190 and the video camera 192, as described in further detail hereinbelow.

In the example, pressure applied by the user's arm 150 muscle—as measured by the pressure meter 152, changes in the arm's 150 orientation—as measured by the orientation measurer 151, or both, are used by the user to control the physical activity monitoring device, even while the user's hands are busy rowing.

Further, orientations and pressures that are within limits set as reference values calculated for rowing, using values extracted from measurements of previous physical activities of rowing by the user, are not erroneously recognized as the predefined gesture, and as a result, do not control the physical activity monitoring device.

Further in the example, GPS data generated by the orientation measurer 151 may be transmitted to the controller 191, and used by the controller 191, to maneuver the quadcopter 190. The GPS data may be used by the controller 191, to maneuver the quadcopter 190, so as to have the quadcopter 190 follow the rafting canoe, down a river, from above, as described in further detail hereinbelow.

In the example, throughout the rafting, both of the user's arms are busy rowing the canoe. However, when arriving at a certain segment of the river, the user spontaneously wishes to have the video camera 192 take video images around the canoe.

To that end, the user changes the tension of the muscle of the user's arm 150—say by twice repeating a strengthening and weakening of the user's grip over the canoe's paddle, by changing the angle of the grip, etc.

The muscle tension changes are sensed by the pressure meter 152 which continuously measures the pressure applied by the muscle of the arm 150.

Based on the changes sensed by the pressure meter 152, the computer processor 153 extracts values, and forwards the extracted values to the value receiver 110 of apparatus 1000.

Then, using the received values, the deviation detector 120 detects a deviation of the user's physical activity from the previous physical activities, and issued a control instruction for the controller 191 to initiate a zoom-in and image capture operation of the video camera 192 and to maneuver the quadcopter 190 so as to fly in a circle over the user.

When receiving the control instruction, the controller 191 immediately actuates the camera 192 to zoom in on the user, and controls the quadcopter's 190 rotor engines, so as to maneuver the quadcopter 190 to fly in a circle over the user.

Figure 2A:
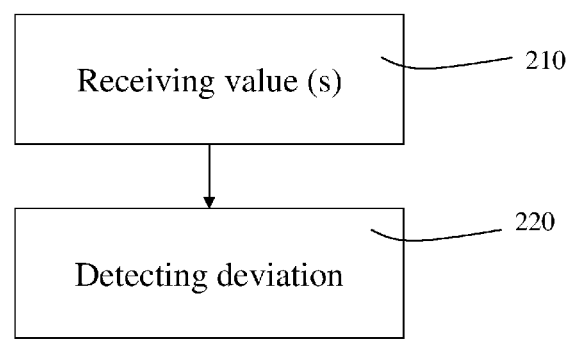

Reference is now made to FIG. 2A, which is a simplified flowchart schematically illustrating a first exemplary method of physical activity measurement and analysis, according to an exemplary embodiment of the present invention.

The first exemplary method may be implemented on a computer, say on the computer of apparatus 1000, as described in further detail hereinabove.

The computer may include, but is not limited to: a computer in a clinical environment such as a physiotherapy clinic or a hospital's neurological department, a computer in use at a gym or at another sport facility, a user's desktop computer, smart phone, tablet, or laptop computer, etc., as described in further detail hereinabove.

Optionally, for carrying out one or more of the method's steps, the computer communicates with a device used to measure a physical activity of a user, for receiving 210 values extracted from measurements of the physical activity, as described in further detail hereinabove.

In the exemplary method, there is thus received 210 one or more values extracted from measurements of a physical activity of a first user, say by the value receiver 110 of apparatus 1000, as described in further detail hereinabove.

The physical activity may include, but is not limited to, walking, running, swimming, biking, skiing, rowing, skating, dancing, operating a mechanical device used for physiotherapy or for exercising in gym, resting (say sitting), operating computer mouse, etc., as described in further detail hereinbelow.

Optionally, the values are received 210 through communication with a device used to take measurements of physical parameters such as pressure applied by a muscle of the first user, orientation of the first user's foot or arm, etc., during the physical activity of the first user, thus measuring the physical activity of the first user.

Optionally, the device measures the physical activity without direct contact with the first user's body (say using one or more cameras and an automatic image processing based analysis of the first user's movements during the physical activity, as known in the art).

Optionally, the measurements that the received 210 values are extracted from are rather taken by a device deployed on a body part of the first user during the physical activity of the first user, as described in further detail hereinabove.

Thus, in one example, the device communicated with is worn by the user during the physical activity. In the example, the device includes one or more sensors (say a pressure meter such as an FSR (Force Sensitive Resistor), a gyroscope, an accelerometer, an IMU (Inertial Measurement Unit), etc.), as described in further detail hereinabove.

In the example, the device worn by the first user may be used to measure the first user's physical activity by taking measurements of pressure applied by an arm muscle of the first, measurements of angular orientation of the first user's arm or foot, etc., during the physical activity, thus extracting the values, as described in further detail hereinabove.

Optionally, the received 210 values include results of each measurement taken by the device during the physical activity (say the result of each measured pressure, orientation, etc., as taken by the device worn by the first user), as described in further detail hereinabove.

Alternatively or additionally, the received 210 values include values calculated (and thus extracted) by the device from the results (say values calculated by the device worn by the user), as described in further detail hereinabove.

Thus, in one example, each one of the received 210 values is an average calculated by the worn device from measurements taken during a respective three minutes period of the physical activity, from two or more measurements taken on the first user's body during that three minutes period.

Later, when found 220 to be the case, there is detected 220 a deviation of the physical activity of the first user from at least one previous physical activity, say by the deviation detector 120 of apparatus 1000, as described in further detail hereinabove.

The deviation is detected 220 using the received 210 one or more values and one or more reference values calculated over at least one value extracted from measurements of the at least one previous physical activity, say according to a predefined criterion, as described in further detail hereinbelow.

Optionally, the criterion, one or more reference values, or both, are selected automatically, say according to the first user's identity (say username, patient number, etc.), the physical activity's type, per a selection made by the administrator using a GUI, etc., or any combination thereof.

Optionally, the criterion is defined by an administrator or programmer of apparatus 1000 in advance of receiving 210 the values, say as a part of setting up the apparatus 1000 (say using a GUI) or programming the computer of the apparatus 1000, as described in further detail hereinbelow.

Per the definition by the administrator or programmer, the criterion may be specific to a user, to a type of a physical activity, to a combination of user and physical activity type, or rather be more general. Accordingly, the criterion may be selected by the deviation detector 120, according to the user, the type of the physical activity, or both, as described in further detail hereinabove.

For example, the administrator may define a user-specific criterion according to which, any deviation of a value received 210 for 'John Man' that is 10% lower or higher than a reference value calculated per physical activity type, is to trigger a detection 220 of a deviation of the physical activity from previous physical activities.

In the example, a deviation of a physical activity (say a Kickboxing Session) by John Man from previous physical activities of a same type (say also of Kickboxing but by other users) may thus be detected 220 based on one of the values received 210 during John Man's physical activity being 11% lower than the reference value.

Accordingly, when values extracted from a physical activity by John Man are received 210, the user-specific criterion pertaining to values received 210 for 'John Man' is automatically selected and may serve as a basis for detecting 220 a deviation of John Man's activity from the previous physical activities.

Optionally, the one or more previous physical activities that the deviation may be detected 220 from, are previous physical activities of the first user (i.e. of the same user).

For example, the measurements of the one or more previous physical activities may be measurements taken on a body part of the first user during the one or more previous physical activity, say using a device similar to the device worn by the user, as described in further detail hereinabove.

Thus, in a first example, the first user's physical activity is one of working with a specific object (say a specific weight) in a gym, as known in art.

In the first example, according to the predefined criterion, the deviation is detected 220 when one of the received 210 values is at least 20% higher than a reference value calculated by averaging over pressure values measured on an arm muscle of the first user during previous exercises with the same object.

Optionally, the reference value is a threshold value. The threshold value may represent a minimal limit or a maximal limit for the received 210 values. Accordingly, in order for the deviation to be detected 220, one of the received 210 values needs to be lower or higher than the reference value, respectively.

Optionally, the physical activity that the received 210 values are extracted from the measurements of, and the previous physical activities are separate—say two or more activities performed on different days, during different physiotherapy sessions, etc.

Optionally, the physical activity that the received 210 values are extracted from the measurements of and the previous physical activities are rather parts of a single physical activity—say a later part and a former part of a single marathon, training session, exercise, etc.

Optionally, the previous physical activity involves a repeated cycle of movement, and each one of the reference values pertains to a different time (say a different time frame) within that cycle of movement that is repeated through the previous physical activity.

Thus, in one example, the physical activity is an indoor cycling session taken by the first user, and the previous physical activities are previous indoor cycling sessions taken by the first user (i.e. by the same user).

In the example, the deviation is detected 220 when one of the received 210 values is out of an "envelope" made of reference values calculated over the previous indoor cycling sessions taken by the first user—say when one of the received 210 values deviates from one of the reference values that make up the envelope, as described in further detail hereinbelow.

Optionally, the one or more reference values are values calculated over a plurality of values extracted from measurements of physical activities of a plurality of users, say over values extracted from measurements taken during previous physical activities of a same type by other users or by both the first user and other users.

Optionally, the reference values are calculated based on reference values extracted from measurements taken on the first user's body using more than one sensor, as described in further detail hereinbelow.

In one example, the physical activity is one of exercising using an object (say a weight) or a device (say a rowing machine) in a gym or a at physiotherapy clinic, and the reference values are calculated over values extracted from measurements of exercises by previous users using that object or device.

Optionally, upon the detection 220 of the deviation, there is issued a predefined command to a computer (say a command defined in advance of the physical activity, say by a programmer or administrator of apparatus 1000), say by the command generator of apparatus 1000, as described in further detail hereinabove.

Optionally, only when the deviation is detected 220, are the received 210 values used for determining whether the received 210 values represent a predefined gesture (say a gesture defined earlier by an administrator of apparatus 1000 using a GUI), say by the gesture recognizer, as described in further detail hereinabove.

Optionally, for defining the gesture, there are defined ranges of values (say ranges of pressure values, orientation values, etc.) that the received 210 values have to be within, in order for a user's movement made during the physical activity measured for extracting the received 210 values, be recognized as the predefined gesture.

Optionally, for defining the gesture, there are defined one or more threshold values (say for pressure, orientation, etc.) that at least one of the received 210 values has to cross, in order for a user's movement made during the physical activity measured for extracting the received 210 values, be recognized as the gesture.

The threshold value may represent a minimal limit or rather a maximal limit for the received 210 value. Accordingly, in order for the gesture to be detected, the received 210 value needs to be lower than the reference value, or higher than the reference value, respectively.

Optionally, the value ranges, threshold values, or both, are defined by a programmer or administrator of apparatus 1000 and stored in a database of gesture definitions, as described in further detail hereinbelow.

Optionally, as a part of defining the gesture, there is further defined a command that the gesture is meant to trigger the issuance of, say a command to be issued by the command generator of apparatus 1000, as described in further detail hereinabove.

Optionally, upon detection 220 of the deviation (with or without the gesture's being recognized) there is issued a command—say a control instruction issued on the computer of apparatus 1000, for instructing a camera controlled by the computer to capture an image with the camera, as described in further detail hereinabove.

Alternatively, the command is issued only when in addition to the detection 220 of the deviation, the first user's movement is recognized as the predefined gesture meant to trigger the issuance of that command to the computer of the apparatus 1000, as described in further detail hereinabove.

Thus, in one example, the first user wears a device that uses a pressure meter (say an FSR strip), an orientation measurer (say an IMU), or both, to extract the values later received 210 by the value receiver 110, by measuring pressure applied by a muscle on the body part of the first user and an orientation of the body part.

In the example, when the first user performs a predefined gesture such as a specific muscle operation or change in orientation of the body part, the received 210 values extracted from the measured pressure applied by the muscle and orientation of the body part may be used to recognize the gesture performed by the first user.

Thus, in the example, the first user may control the computer using a gesture such as a wrist or arm muscle contraction as used for clicking a computer mouse or as if clicking a computer mouse, a contraction of a foot muscle, an alignment of an arm into a lateral orientation, etc., as described in further detail hereinbelow.

In the example, a device worn by the user uses a pressure meter (say an FSR strip) and an orientation measurer (say an IMU), to take measurements of pressure applied by a muscle on a body part of the first user and of orientation of the body part.

The pressure and orientation change when the user performs the gesture, and as a result, values extracted from the measurements taken by the device worn by the user, reflect the change. The extracted values are wirelessly communicated to the computer of apparatus 1000 and are received 210 by the value receiver 110, as described in further detail hereinabove.

When the first user performs the predefined gesture, the received 210 values are used (say by the gesture recognizer) to recognize the gesture (i.e. to determine that the first user performs the gesture during the physical activity), as described in further detail hereinbelow.

However, in the example, only when there is detected 220 the deviation of the first user's physical activity from the previous physical activity, can the predefined gesture be recognized (say by the gesture recognizer) based on the received 210 values, as described in further detail hereinabove.

Thus, in the example, only a movement with which the physical activity deviates from the previous physical activity may also be recognized as the predefined gesture and as a result, trigger the issuance of the command to the computer, as describe in further detail hereinabove.

Additionally or alternatively, there may be determined that the detected 220 deviation reflects a physical condition of the first user—say an improvement in fitness (as compared with previous physical activities of the same type, say biking sessions by the first user). Optionally, the determination that the detected 220 deviation reflects the physical condition is made by the condition indicator, as described in further detail hereinabove.

Optionally, when determining that the deviation reflects the condition, there is further presented an indication, say as a textual or graphical message presented on a screen of the computer of apparatus 1000 or on a website accessible, say by the condition indicator, as described in further detail hereinabove.

Similarly, in the method, there may be determined that the detected 220 deviation reflects a medical condition—say an early stage of Parkinson's disease (say when the detected 220 deviation pertains to resting). An appropriate textual or graphical message may then be presented, say to a physician on a screen of the computer of apparatus 1000, as described in further detail hereinabove.

In one example, the first user is a professional athlete and the detection 220 of the deviation of the physical activity is based on reference values calculated over measurements made during previous training sessions taken by the first user, during a previous physical activity such as a marathon, a bike cycling event (say a sprint), etc.

Further in the example, there may be recognized a gesture predefined by an administrator or programmer of apparatus 1000, say by the gesture recognizer of the apparatus 1000.

In the example, for implementing the gesture recognizer, a programmer may program the computer to recognize the gesture when a user's arm aligns into a specific lateral orientation and immediately following that alignment, a pressure is applied by the arm's muscle in a specific direction.

Further in the example, the predefined gesture is used by the first user for commanding the computer to capture a picture of the first user, say using a camera connected to the computer, to start or stop a stopwatch, etc.

However, the command is issued only if both a deviation from a 'base level' represented by the reference values is detected 220 (say by the deviation detector 120), and the predefined gesture is recognized (say by the gesture recognizer), as described in further detail hereinabove.

That is to say that the gesture recognizer recognizes a first user's movement as the predefined gesture, only if with that movement, the physical activity of the first user deviates from the previous physical activities by the first user. Indeed, only when the physical activity deviates from the previous physical activities, are the received 210 values forwarded to the gesture recognizer, as described in further detail hereinabove.

Thus, a movement of the first user that does not make the first user's physical activity deviate from the previous physical activities, even when similar to the predefined gesture (say when the received 210 values are within ranges predefined for the gesture), is interpreted as a part of the physical activity rather than the gesture.

In one exemplary case, the physical activity is biking and using the received 210 values, a rotational movement of the first user's foot during the physical activity may be recognized as a predefined rotational gesture. However, as a prerequisite to recognizing the gesture, there must also be detected 220 a deviation of the physical activity from previous physical activities of biking by the first user. More specifically, there must be verified 220 that the received 210 values extracted from the measurements taken during the rotational movement (say the measured values) deviate from the reference values.

In this biking example, the reference values that represent that 'base level' are calculated based on values extracted from measurements taken during previous biking activities of the first user, and that foot movements that are a natural part of pushing the bicycle's paddles are not supposed to deviate from.

In a second example, the first user is a person who suffers from Parkinson's disease.

One of the symptoms of Parkinson's disease is tremor at rest that consists of a shaking or oscillating movement, and usually appears when a person's muscles are relaxed, or at rest, as described in further detail hereinabove.

In the second example, the received 210 values are values extracted from measurements taken during a session in which the first user rests, thus in the example, the measured physical activity is actually a one of resting (say of sitting or lying).

Only when there is detected 220 a deviation based on the received 210 values and a reference value, are the received 210 values subject to a step in which the predefined gesture may by recognized based on the received 210 values, say by the gesture recognizer of apparatus 1000, as described in further detail hereinabove.

Optionally, the predefined gesture is characterized by a combination of a specific orientation of the upper arm and a pressure applied by the upper arm at a specific direction.

In the example, the gesture's definition further includes a command that causes a computer (say the computer of apparatus 1000) to call the nurse, thus the gesture may be used by the first user to instruct the computer to call the nurse, as described in further detail hereinabove.

In the example, one reference value is calculated based on values extracted from measurements of previous physical activities. More specifically, the reference value is calculated based on measurements taken from the first user during the previous sessions, as the first user experiences tremor at rest. For example, the reference value may be calculated by averaging over values extracted from pressure and orientation measurements taken during the previous sessions.

In one case, based on a criterion predefined by an administrator or programmer of apparatus 1000, when one of the values received 210 during the rest is more than 10% larger than the reference value, there is detected 220 a deviation of the physical activity from the previous physical activities.

Based on the detection 220, the received 210 values are forwarded to a step in which there is determined if the received 210 values represent the predefined gesture.

However, in the case, it is assumed that with an unintentional movement that is a part of the user's usual tremor at rest, even when the movement is similar to the gesture in direction, angle, etc., none of the received 210 values is likely to be more than 10% larger than the reference value. The received 210 values that are extracted from unintentional movements during the physical activity are thus negated in as far as recognizing the gesture is concerned.

Thus, when staying within the 10% difference from the reference value, the unintentional movement does not make the physical activity deviate from the previous physical activities of rest. As a result, the received 210 values are not forwarded to the step in which there is determined if the received 210 values represent the predefined gesture. The unintentional movement is thus effectively construed as a one that is within the limits of the tremor usually experienced by the first user at rest and that therefore, should not be construed to be the predefined gesture.

Further in the example, a detected 220 deviation from the "base level" of tremor at rest as represented by the reference value may be interpreted as indicating a condition of the user (say an alleviation of tremor at rest symptoms), say by the condition indicator, as described in further detail hereinabove.

In a third example, the first user is a tennis player whose movements during a tennis match are measured (say using a device worn by the user, as described in further detail hereinabove), and are captured using a video camera controlled by the computer of apparatus 1000.

In the example, only upon both a detection 220 of a deviation of the first user's physical activity (i.e. tennis) from the previous activities (say previous tennis matches) and a recognition of one of a small number of predefined gestures, is a movement as captured in the video recorded by the computer in a video file.

More specifically, in the example, a coach wishes that a video brief made of events of interest to the coach, that occur during the match (say Volley Events, Net events, Smashes, etc.) be prepared automatically by apparatus 1000.

To that end, an administrator of apparatus 1000 may define, for example, a gesture that corresponds to a Volley Event, say by defining a value range for an orientation of a user's arm to be in, in order for the gesture that corresponds to the Volley Event to be recognized.

In the example, the administrator further defines a criterion for detecting 220 any deviation of the user's physical activity from previous physical activities of the user.

The criterion is not user-specific, but is specific for tennis. According to the criterion, a pressure measured on a user's arm must cross a reference value (i.e. a threshold), in order for a deviation of the user's physical activity from previous physical activities of the user to be detected 220.

In the example, the administrator further defines the reference value (say using a GUI) as a value to be calculated by averaging over values extracted from pressure measurements taken on the user's arm during the user's previous physical activities of playing tennis, and multiplying the result of the averaging by 1.30.

Subsequently, only when an arm-muscle-applied pressure measured by the device is higher than 1.30×the average of the values extracted from pressure measurements taken on the user's arm during the user's previous physical activities of playing tennis, is the deviation of the user's physical activity detected 220.

More importantly, only when both an arm movement of the user during the match makes the physical activity be detected 220 as deviating from the previous physical activities, and the user's arm aligns in an orientation that is within the predefined range, is the gesture recognized and the movement recorded in the brief.

Optionally, the method further includes a preliminary step of calculating the reference values from previously received values extracted from one or more previous physical activities, say by the reference value calculator of apparatus 1000, as described in further detail hereinabove. In one example, the reference values are calculated by averaging over the previously received values, as described in further detail hereinabove.

Optionally, the calculated reference values are stored in a database of reference values, say a database implemented on a memory of the computer of the apparatus 1000, as described in further detail hereinabove.

Optionally, whenever receiving 210 values extracted from measurements of a physical activity of the first user, one or more of the reference values is updated based on the recently received 210 values, and stored in the database of reference values, as described in further detail hereinabove.

Optionally, the one or more of the reference values as stored in the database of reference values is updated based on the recently received 210 values in an asynchronous way.

In one example, the database is implemented on a server remote from an area in which the physical activity (say running) takes place, and the database is updated through wireless internet communication, say when the user is not far from a public hotspot.

However, in the example, only a part of the area is covered by public hotspots.

In the example, when the user is in a part of the area that is not covered by any of the hotspots, the reference value is temporarily stored and updated in a buffer. Upon arrival of the first user at a part of the area that is covered by one of the hotspots, the updated value is communicated to the database over the internet, and is used to override the reference value as previously stored in the database.

In one example, the received 210 values are values extracted from measurements of pressure applied by the first user's arm muscle, during the physical activity, and the reference value used for detecting 220 the deviation is an average of previously received values. The previously received values are values extracted from measurements of pressure applied by the first user's arm during the previous physical activities—i.e. from the measurements of the previous physical activities.

In the example, according to a predefined criterion, the deviation is detected 220 whenever one of a received 210 values is at least 20% higher than the reference value calculated by averaging over the values extracted from the measurements of the previous physical activities.

Further in the example, the reference value is re-calculated based on both the reference value's value prior to receipt 210 of the values, and the received 210 values.

According to exemplary embodiments, a reference value may be calculated per user, per physical activity type, per user and physical activity type, etc.

Accordingly, in a first example, the database of reference values is a user-specific database dedicated to the first user only. Further in the example, the reference values in the database are accessible according to the type of physical activity (say running, rowing, resting, etc.), say using indexes, primary keys, foreign keys, etc., as known in the art of computer database design.

In a second example, the database of reference values is not user-specific and rather holds reference values of more than one user. Further in the example, the reference values in the database are accessible according to physical activity type (say running, resting, etc.), user, or user and physical activity type, say using indexes, primary keys, foreign keys, etc., as known in the art of computer database design.

Optionally, the method further includes a step in which data on the detected 220 deviation is added (say by the deviation detector 120) to a database that already stores data on previously detected deviations. The database of detected deviations may be implemented, for example, on a memory of the computer of the apparatus 1000, as described in further detail hereinabove.

Optionally, the database of detected deviations holds only data that pertains to the first user, and is thus a personal, user-specific database that is dedicated to the first user only.

In one example, the data in the database of detected deviations that is dedicated to the first user, is accessible according to the type of physical activity (say running, walking, resting, etc.), say using indexes, primary keys, foreign keys, etc., as known in the art of computer database design.

Optionally, the database of detected deviations holds data that pertains to two or more users, and is thus not user-specific.

In one example, the data in the database of detected deviations that is not user-specific, is accessible according to the type of physical activity (say running, resting, etc.), user, or a combination of user and activity type, say using indexes, primary keys, foreign keys, etc., as known in the art.

In one example, the database of detected deviations is updated with a database record that holds the received 210 value extracted from the first user's physical activity, a reference value used to detect 220 the deviation and the deviation's degree (say a difference or ratio calculated between the former two), etc.

Optionally, the method further includes a step in which the detected 220 deviation is evaluated, say by the deviation evaluator of apparatus 1000, as described in further detail hereinabove.

Thus, in one example, the detected 220 deviation is compared to data stored in the database of detected deviations, for evaluating the detected 220 deviation using data on previously detected deviations that is stored in the database.

For example, when the first user is a patient who suffers from a motor disorder, the detected 220 deviation may be compared to data on deviations previously detected for that first user (say using the degrees of deviation), so as to track the progress of the first user, as described in further detail hereinabove.

Further in the method, the reference values, criterions, etc., may be updated in light of the comparison made with the data on the previously detected deviations, say by conditioning a re-calculation of one of the reference values upon a specific trend of change in the deviation's degree, as described in further detail hereinabove.

Thus, in one example, a criterion used by deviation detector 110 is updated in light of a trend made of three consecutive increases in the deviation's degree, say by lowering a percentage of difference from a reference value that is needed for a deviation from the previous activity to be detected according to the criterion.

By updating the criterion, there is further adjusted a sensitivity of the method to the received 210 values (and thus to the measurements) in light of the evaluation of the detected 220 deviations, as described in further detail hereinabove.

Figure 2B:
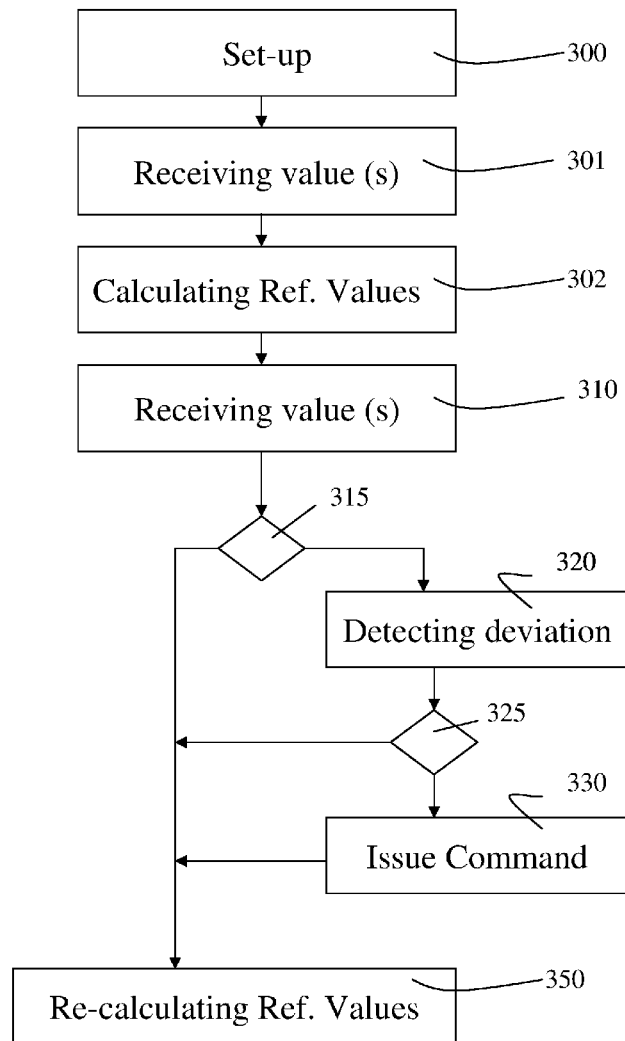

Reference is now made to FIG. 2B, which is a simplified flowchart schematically illustrating a second exemplary method of physical activity measurement and analysis, according to an exemplary embodiment of the present invention.

The second exemplary method may be implemented on a computer, say on the computer of apparatus 1000, as described in further detail hereinabove.

The computer may include, but is not limited to: a computer in a clinical environment such as a physiotherapy clinic or a hospital's neurological department, a computer in use at a gym or at another sport facility, a user's desktop computer, smart phone, tablet, or laptop computer, etc., as described in further detail hereinabove.

In a set-up step 300 of the second exemplary method, there is defined one or more criterions to be used as a basis for detecting 320 a deviation of a physical activity of a user from one or more previous physical activities, say by an administrator of apparatus 1000, as described in further detail hereinabove.

The criterions may be stored in a dedicated database, be embedded in computer code used to implement the method, etc., or any combination thereof, as described in further detail hereinabove.

Optionally, in the set-up step 300, there is further defined a command (say a control instruction) to be issued upon detection of the deviation, as described in further detail hereinabove. The command may be stored in a dedicated database, embedded in computer code used to implement the method, etc., or any combination thereof, as described in further detail hereinabove.

Optionally, in the set-up step 300, there is further defined gesture recognition data—say threshold values or value ranges for a user's movement made during a physical activity to be recognized as the gesture, as described in further detail hereinabove. The gesture recognition data may be stored in a dedicated database, embedded in computer code used to implement the method, etc., or any combination thereof, as described in further detail hereinabove.

Optionally, the gesture definition data further specifies a command to be issued upon recognizing a user's movement during a physical activity of the user as the predefined gesture, as described in further detail hereinabove.

Optionally, in the set-up step 300, there are further defined criterions to be used as a basis for providing an indication on a user's condition (say on a computer screen or a web page), based on the detected 320 deviation of the user's physical activity, as described in further detail hereinabove. The criterions may be stored in a dedicated database, be embedded in computer code used for implementing the method, etc., or any combination thereof, as described in further detail hereinabove.

Next, during a preliminary learning period, for each one of several physical activities, there are received 301 one or more values extracted from measurements of the physical activity, say from measurements of pressure and orientation, as taken on a body part of the user, as described in further detail hereinabove.

Based on the received 301 values, there are calculated 302 one of more reference values, and stored 302, say in a database of reference values, as described in further detail hereinabove.

Optionally, the calculated 302 reference values include thresholds values, value ranges, or both, that serve as a kind of a "base level" of "normal limits" for values extracted from measurements of a physical activity, as expected based on the previous physical activities, as described in further detail hereinabove.

The threshold values and value ranges define "borderlines" for "normal" values extracted from measurements of a physical activity that are made using a single sensor or rather using two or more similar or different sensors that work in unison.

In one example, the values are extracted from measurements taken using an accelerometer and a gyroscope, to give sets of three eight bit values, each of which sets represents a body part's directional and angular speed, as well as the body part's orientation, during a respective time of measurement.

In the example, one of the calculated 302 reference value may be a set of three value ranges. Each one of the three value ranges limits a respective one of the three eight bit values. Accordingly, when 310 received later, a deviation of one of three values extracted from a later physical activity from the respective value range is a basis for detection 320 of a deviation from previous physical activities, as described in further detail hereinbelow.

Optionally, at least some of the calculated 302 reference values make up an "envelope" that serves as a kind of a "base level" of "normal limits" for values extracted from measurements of a physical activity, as expected based on the previous physical activities, as described in further detail hereinabove.

The "envelope" is made of two or more reference values that may include threshold values, value ranges, or both. Each of the reference values is mapped to a specific time frame within a cycle repeated through a physical activity. The "envelope" thus adds a time dimension to the reference values and represents a flow of reference values along the time period of the cycle.

For example, one exemplary "envelope" that pertains to biking, may include a series of value ranges for pressure measured on a foot of a bicycle biker when biking, each of which ranges pertains to a different time frame within a cycle of pressure changes expected to repeat during the biking.

Indeed, when riding a bicycle, a bike paddle completes a full cycle every few seconds, say every seven seconds. In the cycle, when starting with a peak, there is a push downwards using body weight as well as foot muscle. Then, there is a relaxation period that starts when the paddle reaches the lowest point and ends when the paddle is back at the peak.

An exemplary "envelope" of reference values for such a biking activity, may thus include seven value ranges—one value range per each one second long time frame within the seven seconds long cycle. The ranges may pertain to pressure applied by the foot muscle, to an orientation of the foot, or to both, as described in further detail hereinabove.

Optionally, one or more of the value ranges are calculated 302 by calculating an average and a standard deviation over two or more of the received 301 values and using the average and standard deviation to define a minimum and maximum for the value range, as known in the art.

Optionally, one or more of the reference values are calculated 302 by running a linear regression or another approximation technique on the received 301 values, as known in the art. As a result, there may be yielded a series of threshold values or value ranges that make up an "envelope", as described in further detail hereinabove.

The reference values may be calculated 302 per user, per physical activity type, per a combination of user and physical activity type, per time or a time frame within a cycle that one of the "envelopes" pertains too, etc., or any combination thereof, as described in further detail hereinabove.

Later, a first user activity may be measured, say using a device worn on a body part of the first user, as described in further detail hereinabove.

As the first user is engaged in the physical activity, there are received 310 one or more values extracted from measurements of the physical activity, say by the value receiver 110 of apparatus 1000.

In one example, the values are extracted from measurements of pressure and orientation, as taken on the first user's body part (say foot) by the device worn by the user, and are wirelessly communicated to the value receiver 110, as described in further detail hereinabove.

Then, the received 310 values are compared 315 to one or more of the calculated 302 reference values, and based on that comparison 315, there may be detected 320 a deviation of the first user's physical activity from previous physical activities, as described in further detail hereinabove.

For example, when the physical activity is one of biking, each one of the received 310 values is compared 315 to a respective one of the reference values that make up the "envelope", as described in further detail hereinabove.

More specifically, in the example, based on time of receipt 310 of each respective one of the values, the received 310 value is mapped to a respective one of the reference values that make up that "envelope". The "envelope" represents a flow of reference values that is repeated over through the time of the physical activity, as described in further detail hereinabove.

When one of the received 310 values deviates from the respective reference value, there is detected 320 a deviation of the first user's physical activity from the previous physical activities, as described in further detail hereinabove.

In one example, the "envelope" spans a cycle of three minutes (i.e. 180 seconds) and includes eighteen reference values that are evenly spread along the time period of the cycle, such that each one of the reference values pertains to a respective ten seconds long time frame within the cycle.

In the example, the values are received 310 through a period of six minutes, and are accordingly mapped to two consecutive repeats of that "envelope".

Accordingly, a value received 310 in the first or ninety-first second from beginning of the first user's physical activity is compared 315 to the first reference value in that envelope, whereas a value received 310 in the 12th or 102nd second from the beginning is compared 315 to the second reference value in that envelope.

Optionally, upon detection 320 of the deviation based on that comparison 315, there is issued a predefined command (say a control instruction that turns on a camera, for capturing a digital image of the first user), as described in further detail hereinabove.

Alternatively, when there is detected 320 the deviation of the physical activity from the previous physical activities, the received 310 values are used to determine 325 if a movement made by the user during the physical activity should be recognized as one of the predefined gestures. In that way, only when, in addition to the detection 320 of the deviation, there is also determined 325 that indeed, the predefined gesture is made by the user, is a computer command issued 330.

The deviation's detection 320 may thus add a layer to the measured activity, that allows the user to control a device such as smart phone, quadcopter, smart watch, camera, etc., that is controlled by a computer that implants the method or that includes the computer, without stopping the activity, as described in further detail hereinabove.

Optionally, the detection 320 of the deviation further serves to as a basis for following changes in the first user's condition (say an improvement or a deterioration of motor disorder symptoms), and for proving an indication on the first user's condition, say by the condition indicator, as described in further detail hereinabove.

Optionally, the received 310 values are also used for re-calculating 350 one or more of the reference value using both the recently received 310 values and previously received 301 values, or rather using the recently received 310 values and the reference values as calculated 302 prior to that receipt 310.

As a result of the re-calculation 350, the reference values may be updated and recalibrated with each receipt 310 of values extracted from a newer physical activity of the first user, thus allowing a taking into account of physical changes in the user's physical condition and abilities. The reference values may thus remain up-to-date and be useful for monitoring changes (say by the first user's physician or physiotherapist) between physical activities, through long time periods.

Optionally, the method further includes updating a database of detected deviations with data on the detected 320 deviation, and an evaluation of the detected 320 deviation in light of data on previously detected deviations retrieved from that database, as described in further detail hereinabove.

For example, an increasing degree of deviation may indicate an improvement in quality of the first user's intentional motor activity quality.

Further in the method, the reference values, criterions, etc., may be updated in light of the comparison made with the data on the previously detected deviations. For example, a re-calculation 350 of one of the reference values may be conditioned upon a trend of changes in the degree of deviation, say upon the degree's increasing for a third time in a row, as described in further detail hereinabove.

Figure 3:
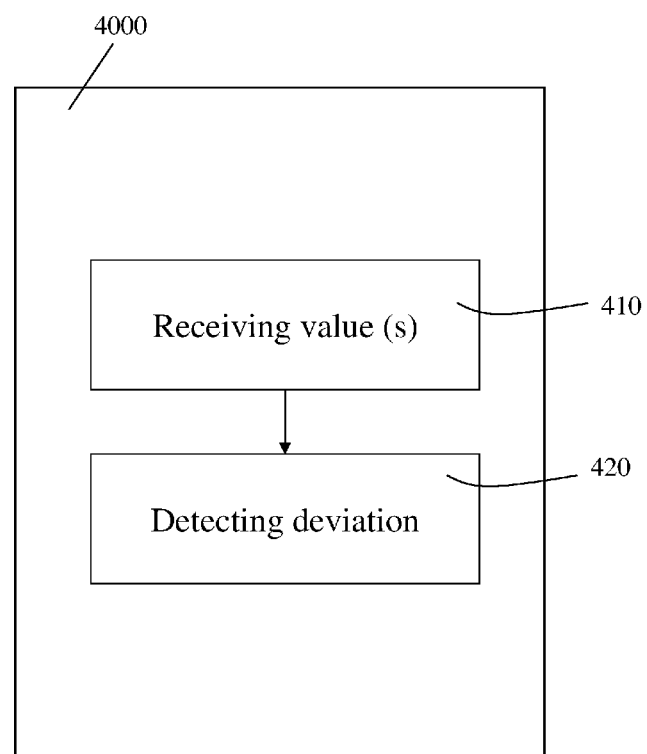

Reference is now made to FIG. 3, which is a block diagram schematically illustrating a non-transitory computer readable medium storing computer executable instructions for performing steps of physical activity measurement and analysis, according to an exemplary embodiment of the present invention.

According to an exemplary embodiment of the present invention, there is provided a non-transitory computer readable medium 4000, such as a Micro SD (Secure Digital) Card, a CD-ROM, a USB-Memory, a Hard Disk Drive (HDD), a Solid State Drive (SSD), etc.

The computer readable medium 4000 stores computer executable instructions, for performing steps of physical activity measurement and analysis, according to an exemplary embodiment of the present invention, say the steps illustrated using FIG. 2A, as described in further detail hereinabove.

Thus, the computer executable instructions include a step of receiving 410 one or more values extracted from measurements of a physical activity of a first user, as described in further detail hereinabove.

The physical activity may include, but is not limited to: walking, running, swimming, biking, skiing, rowing, skating, dancing, operating a mechanical device used for physiotherapy or for exercising in gym, resting (say sitting), operating a computer mouse, etc., as described in further detail hereinbelow.

Optionally, the values are received 410 through communication with a device used to take measurements of physical parameters such as pressure applied by a muscle of the first user, orientation of the first user's foot or hand, etc., during the physical activity of the first user, thus measuring the physical activity of the user.

Optionally, the device measures the physical activity without direct contact with the user's body (say using one or more cameras and an automatic image processing based analysis of the user's movements during the physical activity, as known in the art), as described in further detail hereinabove.

Optionally, the measurements that the received 410 values are extracted from are rather taken by a device deployed on a body part of the first user during the physical activity of the first user, as described in further detail hereinabove.

Thus, in one example, the device communicated with is a device worn by the user during the physical activity. In the example, the device includes one or more sensors (say pressure meters such as an FSR (Force Sensitive Resistor), a gyroscope, an accelerometer, an IMU (Inertial Measurement Unit), etc., or any combination thereof) that are used for measuring the physical activity.

In the example, the device worn by the first user may be used to measure the first user's physical activity by taking measurements of pressure applied by muscle of the first user when extending an arm or a foot, by taking measurements of angular orientation of the first user's arm or foot, etc., during the physical activity.

Optionally, the received 410 values include results of each measurement taken by the device (say the result of each measured pressure, orientation, etc., as taken by the device worn by the user).

Alternatively or additionally, the received 410 values include values calculated by the device from the results (say values calculated by the device worn by the user), as described in further detail hereinabove.

Thus, in one example, each one of the received 410 values is an average calculated by the worn device from measurements taken during a respective three minutes period of the physical activity, from two or more measurements taken on the first user's body during the respective three minutes period.

The computer executable instructions further include a step of detecting 420 a deviation of the physical activity of the first user from at least one previous physical activity (when found 420 to be a case of deviation), as described in further detail hereinabove.

According to the instructions, the deviation is detected 420 using the received 410 one or more values and one or more reference values calculated over at least one value extracted from measurements of the at least one previous physical activity, say according to a predefined criterion, as described in further detail hereinabove.

Optionally, the instructions further include a preliminary step of allowing a user or an administrator of the computer to define the criterion in advance of the receipt 410 of the values, as described in further detail hereinabove.

Optionally, the one or more previous physical activities are previous physical activities of the first user (i.e. of the same user).

Optionally, the measurements of the previous physical activity are measurements taken on a body part of the first user during the previous physical activity, say using one or more sensors of a device similar to the device worn by the user, as described in further detail hereinabove.

Thus, in a first example, the first user's physical activity is one of working with a specific object (say a specific weight) in a gym, as known in art.

In the first example, according to the predefined criterion, the deviation is detected 420 when one of the received 410 values is at least 20% higher than a reference value calculated by averaging over pressure values measured on an arm muscle of the first user during previous exercises with the same object.

Optionally, the physical activity involves a repeated cycle of movement, and each one of the reference values pertains to a different time frame within the repeated cycle of movement, as described in further detail hereinabove.

Thus, in one example, the physical activity is an indoor cycling session taken by the first user, and the previous physical activities are previous indoor cycling sessions taken by the first user.

In the example, the deviation is detected 420 when one of the received 410 values is out of an "envelope" made of reference values calculated over the previous indoor cycling sessions taken by the first user, as described in further detail hereinabove.

Optionally, the one or more reference values are value ranges calculated over a plurality of values extracted from measurements of physical activities of a plurality of users. For example, the value ranges may be calculated by averaging over values extracted from measurements taken during previous physical activities of a same type by other users or by both the first user and other users, as described in further detail hereinabove.

Thus, in one example, the physical activity is one of exercising using an object (say a weight) or a device (say a rowing machine) in a gym or a at physiotherapy clinic, and the reference values are calculated over values extracted from measurements of exercises by previous users using that object or device.

Optionally, the computer executable instructions further include a step in which, upon the detection 420 of the deviation, there is issued a predefined command to a computer, say a command to start a stopwatch, as described in further detail hereinabove.

Optionally, the computer executable instructions further include a step in which, when the deviation is detected 420, the received 410 values are used for determining whether the received 410 values represent a predefined gesture, as described in further detail hereinabove.

Optionally, for defining the gesture, there are defined ranges of values (say ranges of pressure values, orientation values, etc.) that the received 410 values have to be within, in order for a user's movement made during the physical activity measured for extracting the received 410 values, be recognized as the predefined gesture.

Optionally, for defining the gesture, there are defined threshold values (say of pressure values, orientation values, etc.) that the received 410 values have to cross, in order for a user's movement made during the physical activity measured for extracting the received 410 values, be recognized as the predefined gesture.

Thus, optionally, the ranges, thresholds, or both, may be defined by a programmer or administrator, say in a database of gesture definitions, as described in further detail hereinabove. Optionally, there is further defined a command that the predefined gesture is meant to trigger the issuance of, as described in further detail hereinabove.

Optionally, the computer executable instructions further includes a step in which, upon detection 420 of the deviation (with or without the gesture's being recognized), there is issued a command—say a control instruction for a controller to turn on a camera, as described in further detail hereinabove.

Alternatively, in the step, the command is issued only if in addition to the detection 420 of the deviation, the first user's movement is recognized (say using the received 410 values) as the predefined gesture meant to trigger the issuance of that command, as described in further detail hereinabove.

Additionally or alternatively, the computer executable instructions include a step of determining that the detected 420 deviation reflects a physical condition of the first user—say an improvement in the first user's fitness, as described in further detail hereinabove.

Similarly, in the step, there may be determined that the detected 420 deviation reflects a medical condition—say an early stage of Parkinson's disease (say when the detected 420 deviation pertains to resting), as described in further detail hereinabove.

Optionally, the computer executable instructions further include a step of presenting an indication, say as a textual or graphical message on a computer screen or a website (say to the first user or his physician) when determining that the deviation reflects the condition, as described in further detail hereinabove.

In a first example, the first user is a professional athlete and the detection 420 of the deviation of the physical activity is based on reference values calculated over measurements made during previous physical activities (say training sessions) by the first user, as described in further detail hereinabove.

In the example, a movement of the first user during the physical activity may be recognized as a predefined gesture used by the first user for commanding the computer to issue a command (say a control instruction that instructs a controller of a camera to capture a picture of the first user with the camera).

However, the command is issued only if both a detection 420 of a deviation of the physical movement as represented by the received 410 values from a previous physical activity of the user's as represented by the reference values, and a recognition of the predefined gesture based on the received 410 values occur.

That is to say that in the example, in order for a first user's movement to be recognized as the predefined gesture, the movement further has to cause the physical activity of the first user to deviate from the previous physical activities by the first user, as described in further detail hereinabove.

A first user's movement that doesn't make the physical activity deviate from the previous physical activities, even when similar to the predefined gesture (say when received 410 values are within ranges predefined for the gesture), is interpreted as a natural part of the physical activity rather than as the predefined gesture In one exemplary case, the physical activity is biking and a rotational movement of the first user's foot is recognized as a predefined rotational gesture, but only if in addition, one of the received 410 values extracted from the measurements taken during the rotational movement deviates from a predefined reference value.

In this biking example, the reference value represent a 'base level' that is calculated based on values extracted from measurements taken during previous biking activities of the first user, and that foot movements that are a natural part of pushing the bicycle's paddles are not supposed to deviate from.

In a second example, the first user is a person who suffers from Parkinson's disease.

One of the symptoms of Parkinson's disease is tremor at rest, as described in further detail hereinabove.

In the second example, the received 410 values are values extracted from measurements taken during a session in which the first user rests, thus in the example, the measured physical activity is actually a one of resting (say of sitting or lying).

Only when there is detected 420 a deviation of the physical activity from the previous physical activities based on the received 410 values and a reference value, are the received 410 values subject to a step in which the predefined gesture may by recognized based on the received 410 values.

Optionally, the predefined gesture is characterized by a specific orientation of the upper arm and a simultaneous pressure applied by the upper arm at a specific direction.

In the example, the gesture's definition further includes a command that causes the computer to call the nurse, thus the gesture may be used by the first user to instruct the computer to call the nurse, as described in further detail hereinabove.

Further in the example, the computer executable instructions include a preliminary step of calculating the reference value based on measurements taken from the first user during previous sessions, as the first user experiences tremor at rest, say by averaging over values extracted from pressure and orientation measurements.

In one case, based on a criterion predefined by an administrator or programmer, when one of the values received 410 during the rest is more than 10% larger than the reference value, there is detected 420 a deviation of the physical activity from the previous physical activities.

Then, the received 410 values are forwarded to a step in which there is determined if the received 410 values represent the predefined gesture.

However, in that case, it is assumed that with an unintentional movement that is a part of the user's usual tremor at rest, even when the movement is similar to the gesture in direction, angle, etc., none of the received 410 values is likely to be more than 10% larger than the reference value.

Thus, when staying within a 10% difference from the reference value, the unintentional movement does not make the physical activity deviate from previous physical activities of resting. As a result, the received 410 values are not forwarded to the step in which there is determined if the received 410 values represent the predefined gesture. The unintentional movement is thus effectively construed as a one that is within the limits of the tremor usually experienced by the first user at rest and therefore, as a one that should not be construed to be the predefined gesture.

Further in the example, the computer executable instructions include a step in which the detected 420 deviation from the "base level" of tremor at rest as represented by the reference values, may be interpreted as indicating a condition of the user (say an alleviation of tremor at rest symptoms).

Optionally, the computer executable instructions further include a preliminary step of calculating the reference from previously received values extracted from one or more previous physical activities, as described in further detail hereinabove. In one example, the reference values are calculated by averaging over the previously received values, as described in further detail hereinabove.

Optionally, the computer executable instruction further include a step of storing the calculated reference values in a database of reference values, say in a database implemented on a memory of the computer, as described in further detail hereinabove.

Optionally, whenever receiving 410 values extracted from measurements of a physical activity of the first user, one or more of the reference values may be updated based on those recently received 410 values, and stored in the database of reference values, as described in further detail hereinabove.

Thus, in one example, the reference value used for detecting 420 the deviation is an average of values previously extracted from physical pressure measurements taken on a body part of the first user during previous physical activities of the first user.

In the example, whenever receiving 410 values extracted from measurements of a physical activity of the first user, the reference value is re-calculated based on both the reference value's value prior to receipt 410 of the values, and the recently received 410 values, and stored in the database of reference values.

With the exemplary computer executable instructions, a reference value may be calculated per user, per physical activity type, per a combination of user and physical activity type, etc., as described in further detail hereinabove.

Accordingly, in a first example, the database of reference values is a user-specific database dedicated to the first user only.

In the first example, the reference values in the database are accessible according to the type of physical activity (say running, rowing, resting, etc.), say using indexes, primary keys, foreign keys, etc., as known in the art of computer database design.

In a second example, the database of reference values is not user-specific and rather holds reference values of more than one user.

In the second example, the reference values in the database are accessible according to physical activity type (say running, walking, resting, etc.), user, or a combination of user and physical activity type, say using indexes, primary keys, foreign keys, etc., as known in the art of computer database design.

Optionally, the computer executable instructions further include a step in which data on the detected 420 deviation is added to a database of detected deviations, say a database that already stores data on previously detected deviations. The database may be implemented, for example, on a memory of a computer, as described in further detail hereinabove.

In one example, the database of detected deviations holds only data that pertains to the first user, and is thus a personal, user-specific database that is dedicated to the first user only.

In the example, the data in the database of detected deviations that is dedicated to the first user, is accessible according to the type of physical activity (say running, walking, resting, etc.), say using indexes, primary keys, foreign keys, etc., as known in the art of computer database design.

In a second example, the database of detected deviations holds data that pertain to two or more users, and is thus not user-specific.

In the second example, the data in the database of detected deviations that is not user-specific, is accessible according to the type of physical activity (say running, resting, etc.), user, or a combination of user and activity type, say using indexes, primary keys, foreign keys, etc., as known in the art.

Thus, optionally, following the detection 420 of the deviation, the database of detected deviations is updated with data on the detected 420 deviation, as described in further detail hereinabove.

This, in one example, the computer executable instructions further include a step of updating the database of detected deviations with a database record that holds one of the received 410 values extracted from the first user's physical activity, one of the reference values used for detecting 420 the deviation, and the deviation's degree.

The degree may be, for example, a difference calculated between the received 410 value and the reference value, a ratio calculated between the received 410 value and the reference value, etc., as described in further detail hereinabove.

Optionally, the computer executable instructions further includes a step of evaluating the detected 420 deviation, as described in further detail hereinabove.

Thus, in one example, the detected 420 deviation is compared to data stored in the database of detected deviations, for evaluating the detected 420 deviation using data on previously detected deviations that is stored in the database, as described in further detail hereinabove.

For example, when the first user is a patient who suffers from a motor disorder, the detected 420 deviation may be compared to data on deviations detected previously for that first user (say using the degrees of deviation), so as to track the progress of the first user, as described in further detail hereinabove.

Optionally, the computer executable instructions further include a step in which the reference values, criterions, etc., are updated in light of the comparison made with the data on the previously detected deviations, as described in further detail hereinabove.

It is expected that during the life of this patent many relevant devices and systems will be developed and the scope of the terms herein, particularly of the terms "Computer", "Sensor", "Camera", "Processor", "Micro SD Card", "CD-"ROM", "USB-Memory", "Hard Disk Drive (HDD)", "Solid State Drive (SSD)", "FSR (Force Sensitive Resistor)", "Gyroscope", "Accelerometer", and "IMU (Inertial Measurement Unit)", is intended to include all such new technologies a priori.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of physical activity measurement and analysis, the method comprising:
   determining a reference value for at least one previous physical activity, wherein the reference value comprises a threshold value and/or a value range, and wherein the reference value is mapped to a time within a movement cycle repeated by the previous physical activity;
   determining an envelope comprising the reference value;
   positioning a wearable device on a body part of a first user, wherein the wearable device comprises at least one of a pressure meter or an orientation measurer;
   measuring, by at least one of the pressure meter or the orientation measurer, first measurements of a physical activity of the first user;
   extracting, by at least one computer processor in communication with the wearable device, at least one value from the first measurements of the physical activity of the first user;
   comparing the at least one value with the reference value of the envelope, wherein the reference value corresponds to the physical activity;
   detecting a deviation of the physical activity of the first user from the previous physical activity based on the at least one value deviating from the reference value; and
   evaluating the deviation using data on at least one previously detected deviation.

2. The method of claim 1, wherein the first measurements are taken by at least one of the pressure meter or the orientation measurer on the body part of the first user during the physical activity of the first user.

3. The method of claim 1, wherein the previous physical activity is a physical activity of the first user.

4. The method of claim 1, wherein second measurements of the previous physical activity are taken by at least one of the pressure meter or the orientation measurer on the body part of the first user during the previous physical activity, wherein the reference value is determined based on the second measurements of the previous physical activity.

5. The method of claim 1, wherein the reference value is calculated over a plurality of values extracted from second measurements of physical activities of a plurality of users.

6. The method of claim 1, further comprising issuing, by the at least one computer processor, a command based on the detecting of the deviation.

7. The method of claim 1, further comprising:
   recognizing a gesture based on the at least one value; and
   issuing, by the at least one computer processor, a command based on (i) the detecting of the deviation and (ii) the recognizing of the gesture.

8. The method of claim 1, further comprising presenting an indication on a condition of the first user based on the detecting of the deviation.

9. The method of claim 1, further comprising updating the reference value based on the at least one value.

10. The method of claim 1, wherein the reference value is calculated per physical activity type.

11. The method of claim 1, wherein the reference value is calculated per user.

12. The method of claim 1, wherein the reference value is calculated per user and physical activity type.

13. The method of claim 1, further comprising updating a database storing data on a plurality of previously detected deviations based on the deviation, wherein the plurality of previously detected deviations comprises the at least one previously detected deviation.

14. The method of claim 1, wherein the envelope comprises a flow of a plurality of reference values in a time period of the movement cycle repeated by the previous physical activity, and wherein the plurality of reference values comprises the reference value.

15. A method of physical activity measurement and analysis, the method comprising:
  determining a reference value for at least one previous physical activity, wherein the reference value comprises a threshold value and/or a value range, and wherein the reference value is mapped to a time within a movement cycle repeated by the previous physical activity;
  determining an envelope comprising the reference value;
  positioning a wearable device on a body part of a first user, wherein the wearable device comprises at least one of a pressure meter or an orientation measurer;
  measuring, by at least one of the pressure meter or the orientation measurer, first measurements of a physical activity of the first user;
  extracting, by at least one computer processor in communication with the wearable device, at least one value extracted from the first measurements of the physical activity of the first user;
  comparing the at least one value with the reference value of the envelope, wherein the reference value corresponds to the physical activity;
  detecting a deviation of the physical activity of the first user from the previous physical activity based on the at least one value deviating from the reference value;
  recognizing a gesture based on the at least one value; and
  issuing, by the at least one computer processor, a command based on (i) the detecting of the deviation and (ii) the recognizing of the gesture.

16. An apparatus for physical activity measurement and analysis, comprising:
  at least one computer processor configured to:
    determine a reference value for at least one previous physical activity, wherein the reference value comprises a threshold value and/or a value range, and wherein the reference value is mapped to a time within a movement cycle repeated by the previous physical activity; and
    determine an envelope comprising the reference value;
  a wearable device in communication with the at least one computer processor and configured for placement on a body part of a first user, wherein the wearable device comprises at least one of a pressure meter or an orientation measurer configured to generate first measurements of a physical activity of the first user;
  a value receiver, implemented on the computer processor, configured to receive at least one value extracted from the first measurements of the physical activity of the first user;
  a deviation detector, in communication with the value receiver, configured to:
    compare the at least one value with the reference value of the envelope, wherein the reference value corresponds to the physical activity; and
    detect a deviation of the physical activity of the first user from the previous physical activity based on the at least one value deviating from the reference value; and
  a deviation evaluator, in communication with the deviation detector, configured to evaluate the deviation using data on at least one previously detected deviation.

17. The apparatus of claim 16, wherein the first measurements are taken by at least one of the pressure meter or the orientation measurer on the body part of the first user during the physical activity of the first user.

18. The apparatus of claim 16, wherein second measurements of the previous physical activity are taken by at least one of the pressure meter or the orientation measurer on the body part of the first user during the previous physical activity, wherein the reference value is determined based on the second measurements of the previous physical activity.

19. The apparatus of claim 16, wherein the at least one computer processor is configured to:
  recognize a gesture based on the at least one value; and
  issue a command based on (i) the detecting of the deviation and (ii) the recognizing of the gesture.

20. The apparatus of claim 16, wherein the envelope comprises a flow of a plurality of reference values in a time period of the movement cycle repeated by the previous physical activity, and wherein the plurality of reference values comprises the reference value.

* * * * *